Figure 1:
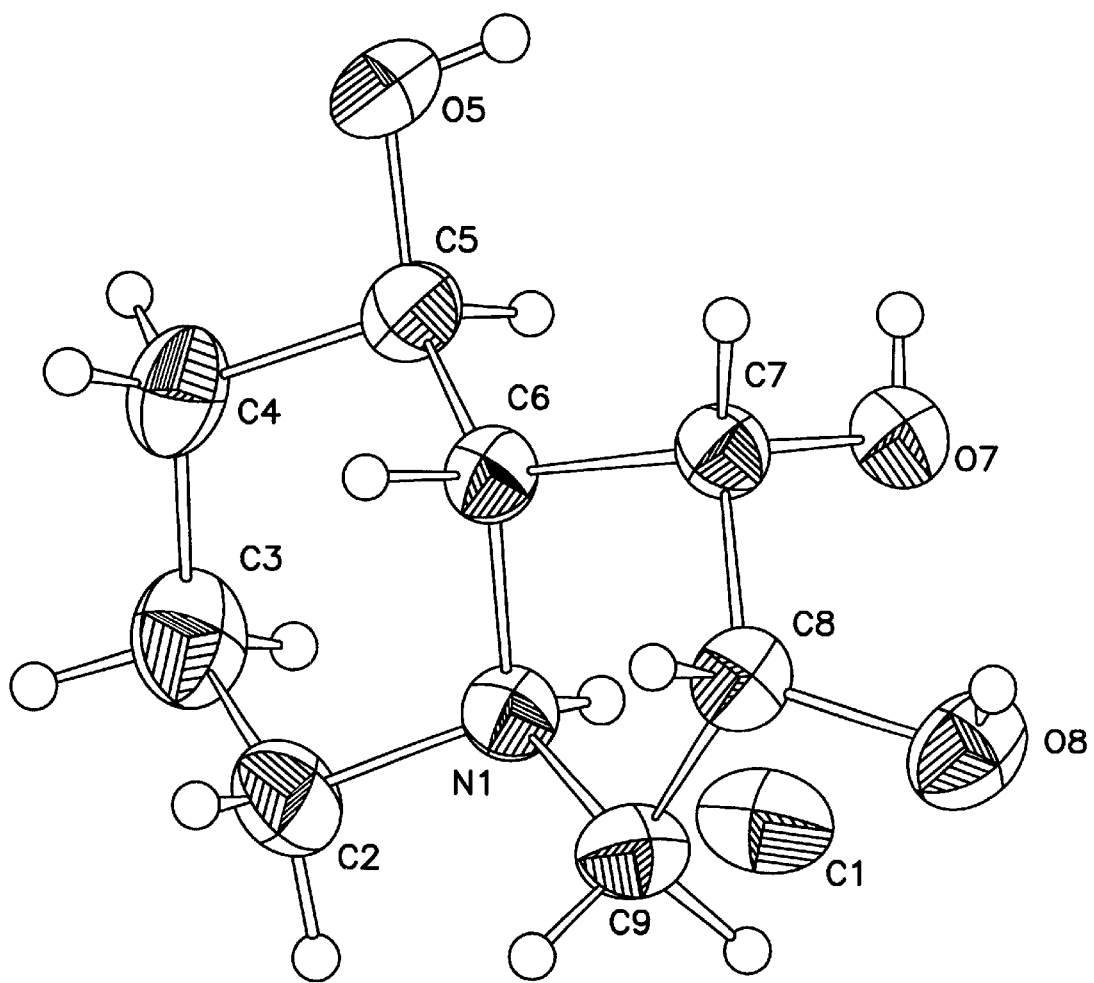
Figure 2:
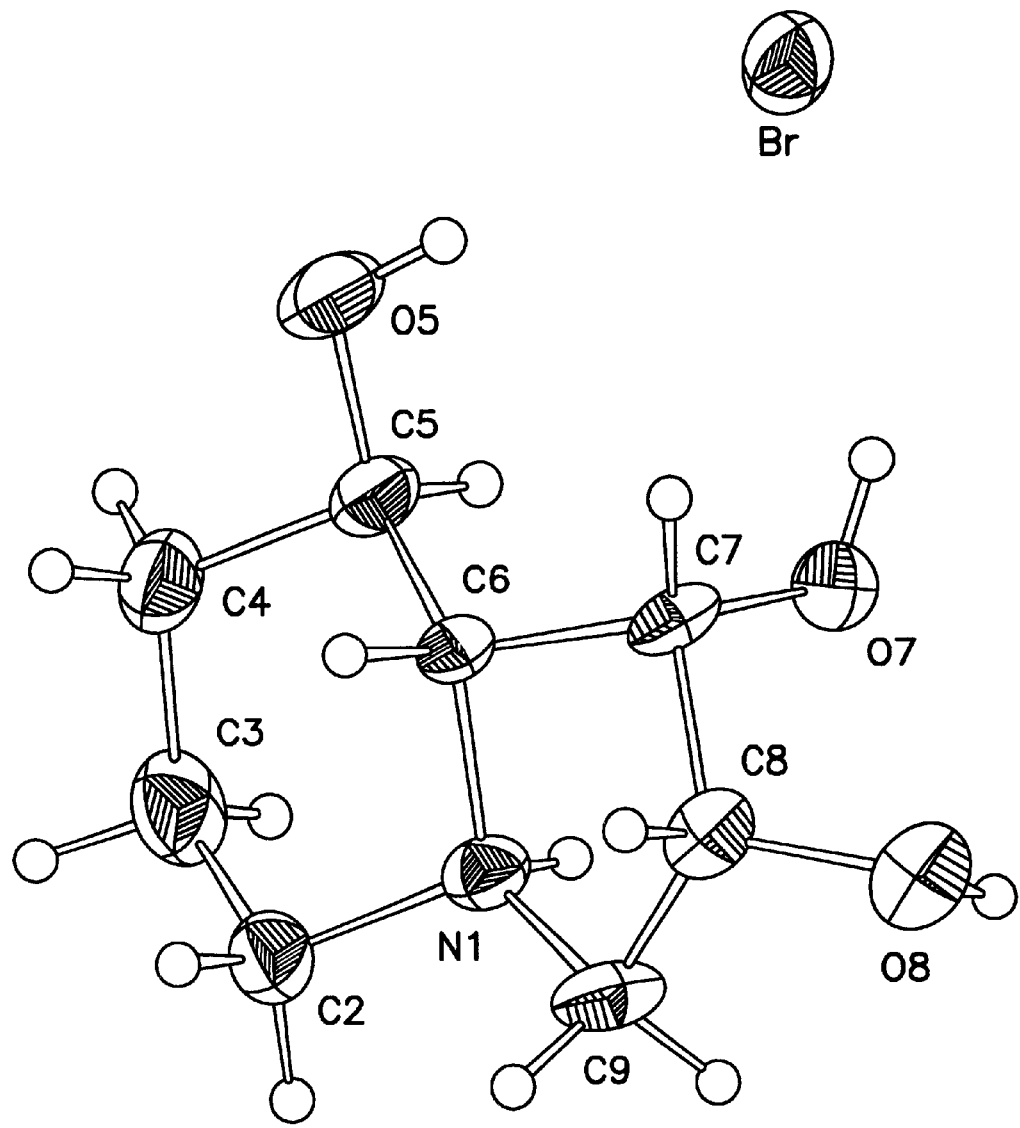
Figure 3:
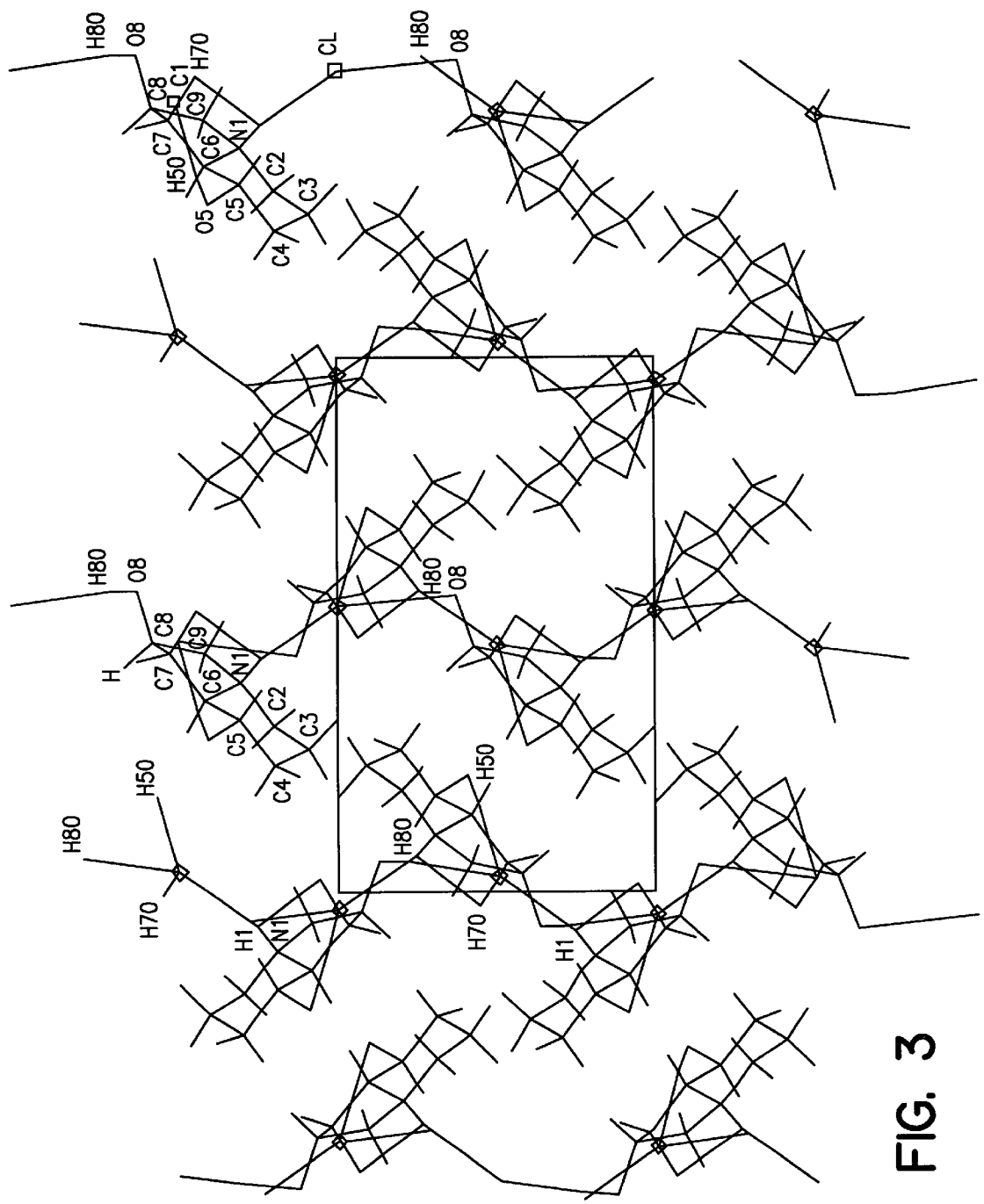
Figure 4:
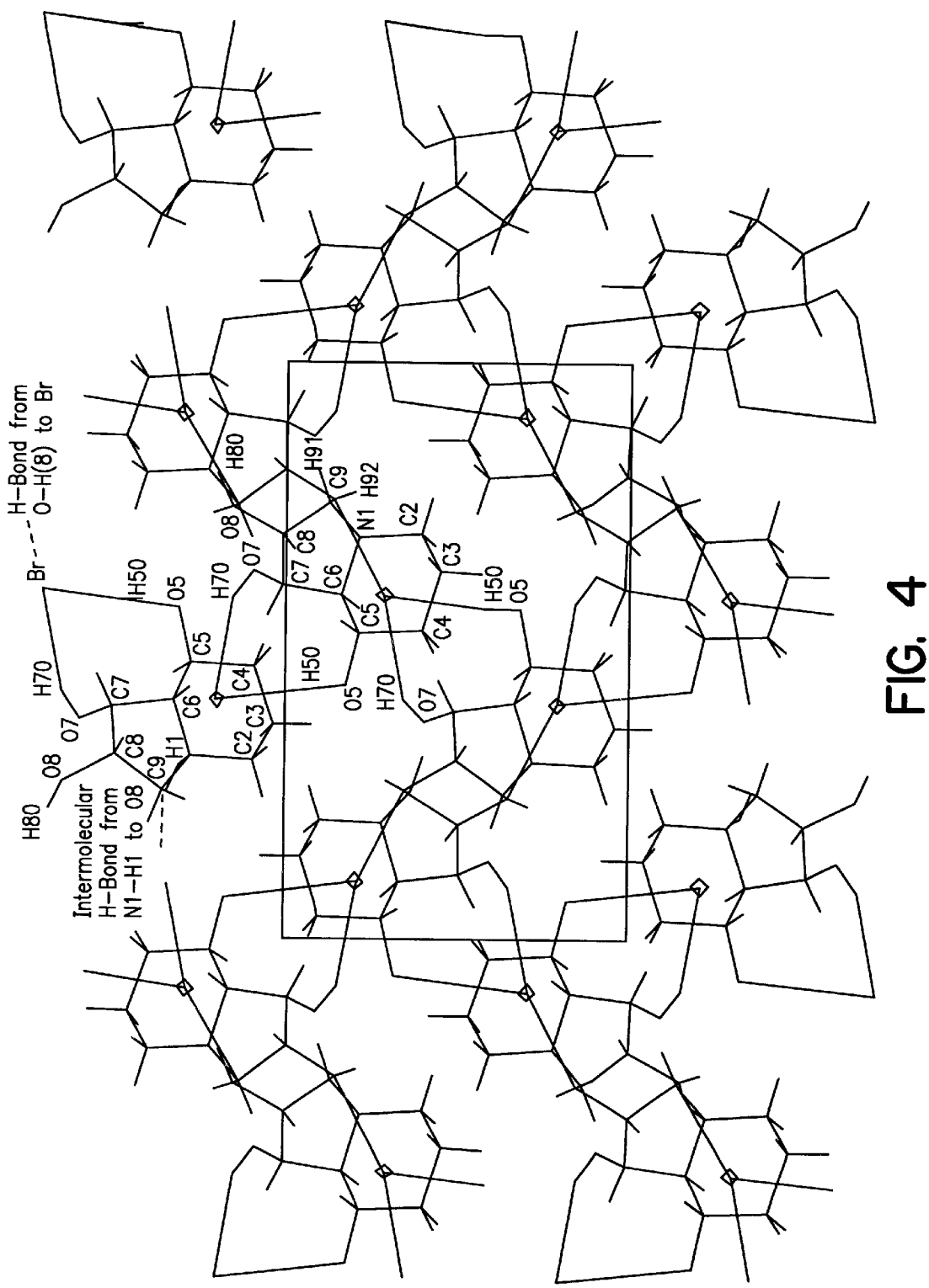

US006395745B1

(12) United States Patent
Dennis et al.

(10) Patent No.: US 6,395,745 B1
(45) Date of Patent: May 28, 2002

(54) ALKALOID HALIDE SALTS OF SWAINSONINE AND METHODS OF USE

(75) Inventors: James W. Dennis, Etobicoke; Rajan N. Shah; Lothar Ziser, both of Toronto, all of (CA)

(73) Assignee: GlycoDesign, Inc. (CA)

( * ) Notice: Subject to any disclaimer, the term of this patent is extended or adjusted under 35 U.S.C. 154(b) by 0 days.

(21) Appl. No.: 09/403,000

(22) PCT Filed: Apr. 15, 1998

(86) PCT No.: PCT/CA98/00360

§ 371 (c)(1),
(2), (4) Date: Mar. 27, 2000

(87) PCT Pub. No.: WO98/46602

PCT Pub. Date: Oct. 22, 1998

Related U.S. Application Data

(60) Provisional application No. 60/086,242, filed on Apr. 15, 1997, and provisional application No. 60/076,426, filed on Feb. 24, 1998.

(51) Int. Cl.$^{7}$ .................................... A61K 31/44
(52) U.S. Cl. .................................... 514/299; 546/183
(58) Field of Search .................................... 546/183; 514/299

(56) References Cited

U.S. PATENT DOCUMENTS

| | | | | |
|---|---|---|---|---|
| 3,274,202 | A | 9/1966 | Mohrbacher | 260/294 |
| 4,792,558 | A | 12/1988 | Sunkara et al. | 514/299 |
| 4,837,237 | A | 6/1989 | Rohrschneider et al. | 514/62 |
| 4,857,315 | A | 8/1989 | Dennis | 424/85.2 |
| 4,894,388 | A | 1/1990 | Fleet | 514/425 |
| 4,996,329 | A | 2/1991 | Fleet et al. | 548/453 |
| 5,021,427 | A | 6/1991 | Elbein et al. | 514/315 |
| 5,023,340 | A | 6/1991 | Fleet | 548/453 |
| 5,041,555 | A | 8/1991 | Fleet et al. | 548/541 |
| 5,075,448 | A | 12/1991 | Fleet | 546/112 |
| 5,075,457 | A | 12/1991 | Fleet | 548/453 |
| 5,187,279 | A | 2/1993 | Cha et al. | 546/183 |
| 5,264,356 | A | 11/1993 | Rohrschneider | 425/236 |
| 5,272,070 | A | 12/1993 | Lehrman et al. | 435/172.1 |
| 5,288,875 | A | 2/1994 | Cha et al. | 548/453 |
| 5,376,675 | A | 12/1994 | Alphey et al. | 514/425 |
| 5,382,709 | A | 1/1995 | Farr et al. | 568/704 |
| 5,438,069 | A | 8/1995 | Farr et al. | 514/1 |
| 5,466,809 | A | 11/1995 | Dime | 546/183 |
| 5,484,925 | A | 1/1996 | Cha et al. | 546/90 |
| 5,621,106 | A | 4/1997 | Dime | 546/183 |
| 5,633,261 | A | 5/1997 | Dime | 514/299 |
| 5,650,413 | A | 7/1997 | Carver et al. | 514/299 |
| 5,780,633 | A | 7/1998 | Okada et al. | 546/112 |
| 5,919,952 | A | 7/1999 | Pearson et al. | |
| 5,962,467 | A | 10/1999 | Carver et al. | |
| 6,048,870 | A | 4/2000 | Shah et at. | |
| 6,051,711 | A | 4/2000 | Tropper et al. | |

FOREIGN PATENT DOCUMENTS

| | | |
|---|---|---|
| CA | 1298549 | 4/1992 |
| DE | 3507019 | 8/1986 |
| EP | 0004260 | 10/1979 |
| EP | 0036269 | 9/1981 |
| EP | 104826 | 4/1984 |
| EP | 295538 | 12/1988 |
| EP | 424349 | 4/1991 |
| EP | 451834 | 10/1991 |
| JP | 60218389 | 4/1984 |
| JP | 60166680 | 8/1985 |
| JP | 60193986 | 10/1985 |
| JP | 61227566 | 9/1986 |
| JP | 61277685 | 12/1986 |
| WO | WO9006311 | 6/1990 |
| WO | WO93/05040 | 3/1993 |
| WO | WO93/05781 | 4/1993 |
| WO | WO9309117 | 5/1993 |
| WO | WO9535094 | 12/1995 |
| WO | WO9640683 | 12/1996 |
| WO | WO9814445 | 4/1998 |
| WO | WO9814446 | 4/1998 |
| WO | 00/37465 | 6/2000 |

OTHER PUBLICATIONS

McInosh JM ; Azapropellanes as Phase transfer Catalysts–II; Tetrahedron vol. 18, No. 2, pp. 261–266 1982.

Reinecke MG; Perifepheral Synthisis of Secondary Medium–Ring Nitrogen Heterocycles : K. Org. Chem., vol. 38 No. 19, pp. 3281–3287, 1973.

Reinecke MG; Perifepheral Synthisis of Secondary Medium–Ring Nitrogen Heterocycles by Displacement Reactions : K. Org. Chem., vol. 37 No. 22, pp. 3494–3498, 1972.

Martin SF; Application of Reductive, Single Electron Transfer Processes to The Generation and Cyclization of Unsaturated Alpha Amino Radicals; Tetrahedron Letters, vol. 29, No. 51, pp. 6685–6688, 1988.

Colegate S.M. et al., Aust. J. Chem. 1979, 32: 2257–64, 1979.

Molyneux R.J. an L.F. James, Science 216:190, Apr. 1982.

Schneider M.J. et al, Tetrahedron 39(1): 29, 1983.

Tulsiani D.R.P. et al, J. Biol. Chem. 257:7936, 1982.

Fernandes, B. et al, Cancer Research 51: 718, 1991.

Dennis J. W. in “Cell Surface Carbohydrates and Cell Development”, Fukuda M.(ed)., CRC Press, Boca Raton, Ann Arbor London, 1992, Chapter 6, pp. 161–194.

Dennis J. W. et al, Science, 236:582, 1987.

VanderElst, E. and J W Dennis, Experimental Cell Research 192: 612–621, 1991.

J. W. Dennis, Cancer Research 46:5131, 1986.

Humphries, M. J. et al, Proc.Natl. Acad. Sci. USA, 83:1752, 1986.

Olden K. et al, Pharmac. Ther. 50:285, 1991.

Humphries, M.J. et al, Cancer Research 48:1410, 1988.

M. Yagita and E. Sakela, Scand. J. Immunol. 31:275–282, 1990.

(List continued on next page.)

*Primary Examiner*—Amelia Owens

(57) ABSTRACT

Crystalline salts of swainsonine, and methods using same.

33 Claims, 13 Drawing Sheets

OTHER PUBLICATIONS

White, S.L. et al, Biochem Biophys. Res. Commun. 150:615–625, 1988.
Seftor, R.E.B. Melanoma Research 1:43–54, 1991.
Yagel S., et al., Intl. J. Cancer 44:685, 1989.
J.W. Dennis et al, J. National Cancer Institute 81:1028, 1989.
J.W. Dennis et al, Cancer Research 50:1867, 1990.
Humphries, M.J. and K. Olden, Pharmac. Ther. 44:85–105, 1989.
White, S.L. et al., Cancer Communications, 3(30):83, 1991.
Oredipe, O.A., et al, J. National Cancer Institute, 83:1149, 1991.
J.W. Dennis, et al, Biochemical Pharmacology 46:1459, 1993.
Aoyama, H. et al, J. Org. Chem. 57: 3037–3041, 1992.
Hibbett, E. P., and J. Sam, J. Het. Chem. 7:857, 1970.
Heidt, P.C. et al, Tetrahedron Letters 31: 5441, 1990.
Reineck, M., and L.R. Kray, J. Org. Chem. 29: 1736, 1964.
Chastanet, J. and G. Roussi, J. Org. Chem, 50:2910–2914, 1985.
Bashyal, B.P. et al, Tetrahedron Letters, 3083, 1987.
Clemo, G.R. and T.P. Metcalfe, J. Chem. Soc. 1937, p. 1518.
Leonard, N.J. et al, J. Org. Chem. 22:1445, 1957.
Winkler D.A. and G. Holan, J. Med. Chem., 32: 2084, 1989.
Reineck, M.G. and L.R. Kray, J. Org. Chem 30:3671, 1965.
Bogeso, K.P. et al, J. Med. Chem. 30:142–150, 1987.
Goss P.E. et al, Cancer Res. 54: 1450, 1994.
Hino et al, J. Antibiot. (Tokyo) 38: 926–935, 1985.
Goss, P.E. et al, Clin. Cancer Res. 3:1077, 1997.
Holden R.T. and R. Raper, J. Chem. Soc. p. 2545, 1963.
Biniecki, S. et al.,Chemical Abstracts, 1984, 101, No. 90743a.
Biniecki, S. et al., Chemical Abstracts, 106, 1987, 138204h.
Boegesoe, K. P., et al., Chemical Abstracts, 106, 1987, No. 84369v.
Smith, M.B. et al., Chemical Abstracts vol. 104, No. 51007f.
Hashimoto, S. et al., Chemical Abstracts vol. 106, 1987, No. 138253y.
Miyano, Se. et al, Chemical Abstracts, vol. 98, 1983, No. 179148c.
Yoon, U.C. et al., Chemical Abstracts vol. 97, 1982, No. 38827r.
Fujiwara, et al, Chemical Abstracts vol. 117, 1992, No. 211862e.
Winterfeld, K. et al., Chemical Abstracts vol. 74, 1971, No. 3456s.
Motohiro, et al., Chemical Abstracts, vol. 101, Abstract 28283x, 1984.
Temple Jr. C. and G. Rener, J. Med Chem 32:2089, 1989.
Nicolson, G.L. Biochem Biophys. Acta. 695:113, 1982.
Tulsiani, D.R.P. et al., Archives Biochem. Biophys. 232: 76–85, 1984.
Levine, A.S. et al., Can. Res. 39: 1645–1650, 1970.
Bowlin, T. L. et al., Cancer Research 49:4109–4113, 1989.
Tulsiani, D.R.P. and O. Touster, J. Biol. Chem., 258: 7578–7585, 1983.
S.R. Wilson and R.A. Sawicki J. Org. Chem 44:330, 1979.
Villiani et al, J. Org. Chem., 6:142, 1962.
Austin, G.N. et al, Tetrahedron 43:3095–3108, 1987.
Skelton, B.W. and White, A.H., Aust. J. Chem. 33:435–9, 1980.
Pearson, W. H. and E.J. Hembre, J. Org. Chem. 61:5546–5556, 1996.
Rodriguez, R. and F. Bermejo, Tetrahedron Letters 37: 5581–5584, 1996.
Keck, G. E. and D.R. Romer, J. Org. Chem. 58: 6083–6089, 1993.
Kim Y.G., and J.K. Cha, Tetrahedron Letters, 30:5721–5724, 1989.
Tadano, K. et al, J. Org Chem., 53:5209–5215, 1988.
Tadano, K., et al., Bull Chem. Soc. Jpn. 59: 3885–3892, 1986.
Tadano, K., et al, Bull. Chem. Soc. Jpn., 60: 3667–3671, 1987.
Honda, T. et al, Chem. Soc. Perkin Trans. 1, p. 2091, 1994.
Suami, T. et al, Chemistry Letters, pp. 513–516, 1984.
Hembre, E.J. and W. H. Pearson, Tetrahedron 53: 11021–11032, 1997.
Fleet, G.W.J. et al., Tetrahedron Letters 26: 3127–3130, 1985.
Fleet, G.W.J. et al, Tetrahedron 44:2649, 1988.
Demetriou M. et al, J. Cell Biol. 130:383–392, 1995.
Dennis et al., Oncogene 4:853–860, 1998.
Bennett R.B. et al, J. Org. Chem. Soc. 111:2580–2582, 1989.
The Alkaloids, vol. 44, Chapter 3, Simple Indolizidine Alkaloids, Hiroki Takahata and Takafumi Momose, 1993 Academic Press.
Miller, Scott. A, and R. Chamberlin A. Am. Chem. Soc. 1990, 112, pp. 8100–8112.
Pearson, W. and Erik J. Hembre, J. Org. Chem 1996, 61, pp. 7217–7221.
Enantiospecific Syntheses of Leukotrienes, $C_4$, $D_4$, and $E_4$, and $[14,15-_3H_2]$ Leukotriene E4 Dimethyl Ester, Cohen et al, 1983 American Chemical Society.
Cohen et al. Org. Synth., (1985) 63,, pp. 127–135.
The Chemistry of Catanospermine, Part IV: Synthetic Modifications at C–8. Furneux et al., Tetraahedron vol. 51, No. 46, pp. 12611–12630, 1995.
Pearson et al, J.Org. Chem. 1996, 61, pp. 5546–5556.
Carpenter et al., Tetrahedron Letters, vol. 30, No. 51, pp. 7261–7264, 1989.

US 6,395,745 B1

ALKALOID HALIDE SALTS OF SWAINSONINE AND METHODS OF USE

This application claims the benefit of the filing date of U.S. Provisional Application Serial No. 60/086,242 filed Apr. 15, 1997 (converted from U.S. Ser. No. 08/840,559) and No. 60/076,426 filed Feb. 24, 1998.

FIELD OF THE INVENTION

The invention relates to halide salts of swainsonine, and methods of using the salts.

BACKGROUND OF THE INVENTION

Swainsonine (SW) is an indolizidine alkaloid which can be isolated from Australian *Swainsona canescens* (Colegate et al., Aust J Chem 32:2257–2264, 1979), North American plants of the genera Astragalus and Oxytropis (Molyneux R J and James L F., Science 215:190–191, 1981), and the fungus *Rhizoctonia leguminicola* (Schneider et al., Tetrahedron 39;29–31, 1983). Swainsonine has interesting immunomodulating and cancer suppression activity which has been attributed to its ability to inhibit α-mannosidase II activity. Swainsonine is believed to function as an enzyme inhibitor because it can mimic the glycosylium cation intermediate generated during the hydrolytic cleavage of mannopyranosides. (Goss, P. E. et al., *Clin. Cancer Res.* 1: 935–944, 1995).

The swainsonine blockage of α-mannosidase II prevents expression of GlcNAc β(1–6) branched N-linked carbohydrates. Swainsonine-treated murine tumor cells have been found to be less metastatic in both organ-colonization and spontaneous metastasis assays in mice (Dennis J. W., Cancer Res. 46:5131–5136, 1986 and Humphries et al., Proc. Natl. Acad. Sci. USA 83:1752–1756, 1986). Swainsonine has also been shown to block tumor cell invasion through extracellular matrix in vitro (Yegel et al., Int. J. Cancer 44:685–690, 1989 and Seftor et al., Melanoma Res. 1:53–54, 1991). Swainsonine administered either orally or by mini-osmotic pumps to athymic nude mice inhibited the growth rate of human MeWo melanoma and HT29m colon carcinoma tumor xenografts in the mice (Dennis et al., J. Natl. Cancer Ins 81:1028–1033, 1989 and Dennis et al., Cancer Res., 50:1867–1872, 1990). Phase I clinical studies of swainsonine in metastatic cancer patients have been completed in Canada (Goss et. al, *Cancer Res.,* 54:1450, 1995 and Goss et al., Clinical Cancer Research, 3:1077, 1997).

Swainsonine has immune stimulatory effects (reviewed in Humphries M. J. and Olden K., Pharmacol Ther. 44:85–105, 1989, and Olden et al., Pharmacol Ther 50:285–290, 1991)). In particular, swainsonine has been shown to alleviate both chemically-induced and tumor-associated immune suppression (Hino et al., J. Antibiot. (Tokyo) 38:926935, 1985), increase NK cell (Humphries et al., Cancer Res. 48:1410–1415, 1988), and LAK cell activities (Yagita M. and Saksela E., Scand. J. Immunol. 31:275–282. 1990), and increase splenic and bone marrow (BM) cell proliferation (White et al., Biochem. Biophys. Res. Commun. 150;615–625, 1988; Bowlin et al. Cancer Res 49, 4109–4113, 1989, and White et al., Cancer Commun. 3:83–91, 1991).

Swainsonine has also been shown to have hemorestorative/chemoprotective effects. For example, swainsonine has been shown to protect against the lethality of various chemotherapeutic agents (Oredipe et al, 1991, Natl. Cancer Inst. 83:1149–1156, 1991). In these studies, enhanced survival in the swainsonine-treated mice correlated with stimulation of bone marrow proliferation, bone marrow cellularity and engraftment efficiency in the mice (Oredipe et al, 1991; White et al, 1991).

U.S. Pat. No. 4,857,315 describes compositions containing SW and active analogues of SW in a pharmaceutical formulation to inhibit cancer metastasis and cell proliferation, and in combination with interferon or an interferon inducer to enhance the antiproliferative and antiviral effects of the interferon or interferon inducer.

SUMMARY OF THE INVENTION

The present invention relates to stable and substantially purified synthetic halide salts of swainsonine. Halide salts may be very difficult to purify in a stable form, and it was uncertain that the swainsonine salts would form crystals that could be used to determine structure by X-ray diffraction. In particular, the present inventors were able to obtain stable and substantially purified crystalline chloride and bromide salts of swainsonine, and determine their structure by X-ray crystallography.

The swainsonine salts of the invention have both in vitro and in vivo anticancer activity. Significantly certain salts of the invention have enhanced stability properties as compared to swainsonine free base, and they have properties which may enable them to dissolve and target faster than swainsonine. Therefore, salts of the present invention provide improved pharmaceutical compositions.

One aspect of the invention resides in obtaining certain halide salts of swainsonine, and in particular in obtaining crystalline chloride and bromide salts of swainsonine of sufficient quality to determine the three dimensional (tertiary) structure of the compounds by X-ray diffraction methods. Accordingly, the invention provides crystals of sufficient quality to obtain a determination of the three-dimensional structure of the chloride and bromide salts of swainsonine to high resolution.

Therefore, the present invention provides stable crystalline chloride and bromide salts of swainsonine. In particular, the invention relates to a stable crystalline chloride or bromide salt of swainsonine comprising molecules of swainsonine chloride or bromide salts in a unit cell held together by hydrogen bond interactions. In an embodiment, the crystalline chloride and bromide salt comprises four molecules of swainsonine chloride or bromide salts in a unit cell. Preferably, the crystalline chloride and bromide salt comprises molecules of swainsonine hydrochloride or hydrobromide salts.

The chloride and bromide salts of swainsonine of the invention, in particular crystalline swainsonine hydrochloride or hydrobromide salts may be used to prepare pharmaceutical compositions. Therefore, the invention provides a method for preparing a pharmaceutical composition comprising mixing a chloride or bromide salt of swainsonine, preferably a crystalline hydrochloride or hydrobromide salt of swainsonine, into a selected pharmaceutical vehicle, excipient or diluent, and optionally adding other therapeutic agents.

The invention also contemplates a composition, in particular a pharmaceutical composition, comprising a swainsonine chloride or bromide salt of the invention, preferably a hydrochloride or hydrobromide salt. In a preferred embodiment of the invention, a solid form pharmaceutical composition is provided (e.g. tablets, capsules, powdered or pulverized form) comprising a crystalline swainsonine hydrochloride or hydrobromide salt.

In vitro and in vivo studies have shown that salts of the present invention, in particular, swainsonine hydrochloride salt of the invention have immunomodulating and cancer suppression properties and hemorestorative/chemoprotective properties. For example, treatment with a swainsonine hydrochloride salt of the invention reduced growth of SP1.A3a mammary adenocarcinoma cells injected in immune competent mice, when administered either by i.p. injection or orally in drinking water. The growth of SP1A3a cells in vitro was stimulated by TGF-β1 and TNFα and these effects were suppressed by swainsonine hydrochloride salt of the invention. In addition, treatment of murine bone marrow cells in vitro with a swainsonine hydrochloride salt of the invention stimulated the proliferation of both erthyroid and granulocyte-macrophage colony forming units (CFU-E and CFU-GM, respectively).

Therefore, the invention still further relates to a method for stimulating the immune system, stimulating hematopoietic progenitor cell growth, treating proliferative disorders or microbial or parasitic infections, or conferring protection against chemotherapy and radiation therapy in a subject comprising administering an effective amount of a swainsonine salt of the invention. The invention also relates to the use of a swainsonine salt of the invention in the preparation of a medicament for stimulating the immune system, stimulating hematopoietic progenitor cell growth, or conferring protection against chemotherapy and radiation therapy in a subject, and/or for treating proliferative disorders, and microbial or parasitic infections.

The knowledge obtained concerning the chloride and bromide salts of swainsonine may be used to model the tertiary structure of related compounds i.e. analogs and derivatives of swainsonine and salts thereof. In addition, the knowledge of the structure of the chloride and bromide salts of swainsonine provides a means of investigating the mechanism of action of these compounds in the body. For example, the ability of compounds to inhibit α-mannosidase II activity may be predicted by various computer models. The knowledge of the atomic coordinates and atomic details of the chloride and bromide salts of swainsonine may be used to design, evaluate computationally, synthesize and use modulators of swainsonine and analogues and derivatives thereof, that prevent or treat any undesirable physical and pharmacological properties of swainsonine. Accordingly, another aspect of the invention is to provide material which is a starting material in the rational design of drugs which mimic the action of halide salts of swainsonine. These drugs may be used as therapies that are beneficial in the treatment of immune and proliferative diseases, or microbial or parasitic infections.

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

The invention will now be described in relation to the drawings in which:

FIG. 1 shows the molecular structure of swainsonine hydrochloride salt;

FIG. 2 shows the molecular structure of swainsonine hydrobromide salt;

FIG. 3 is a crystal packing diagram for swainsonine hydrochloride;

FIG. 4 is a crystal packing diagram for swainsonine hydrobromide;

FIG. 5 is a mass spectrum of a swainsonine hydrochloride salt of the invention;

FIG. 6 is a high performance liquid chromatogram of a swainsonine hydrochloride salt of the invention;

FIG. 7 is a graph showing the effect of swainsonine hydrochloride on proliferation of SP1.A3 a mammary tumor cell proliferation in vitro;

FIG. 8 is a graph showing inhibition of tumor growth by swainsonine hydrochloride via Alzet pump;

FIG. 9 is a graph showing inhibition of tumor growth by oral administration of swainsonine hydrochloride;

FIGS. 10A, 10B and 10C are blots showing that swainsonine hydrochloride increases the activation of STAT1 in spleen following treatment of DBA/2 mice with Poly IC; and FIG. 11 is a graph showing the in vitro effect of swainsonine hydrochloride on murine bone marrow CFU-GM in the presence of different cytokines.

DETAILED DESCRIPTION OF THE INVENTION

Swainsonine Salts of the Invention

The present invention provides stable and substantially purified halide salts of swainsonine. A "halide salt" is a chloride, fluoride, bromide, iodide salt, preferably, a chloride or bromide salt. The counter-cation of the salt can be an alkali metal (e.g. Li, Na, or K), or preferably, hydrogen. In an embodiment of the invention, a hydrochloride salt of swainsonine is provided that has greater thermal stability than swainsonine free base (e.g. it is more stable than swainsonine free base when exposed to atmospheric oxygen or nitrogen:at about 105° C. for about seven days).

In another embodiment, the present invention provides a crystalline chloride or bromide salt of swainsonine. A crystalline chloride or bromide salt of swainsonine may comprise molecules of swainsonine chloride or bromide salts in a unit cell held together by hydrogen bond interactions. In particular, the crystalline chloride or bromide salt comprises four molecules of swainsonine chloride or bromide salts in a unit cell. Preferably the crystalline chloride or bromide salt comprises four molecules of swainsonine hydrochloride or hydrobromide salts in a unit cell.

A crystalline swainsonine chloride salt of the invention may be held together by hydrogen bond interactions from the protonated nitrogen and hydroxyl oxygen atoms of a molecule of a swainsonine chloride salt to chloride ions of other molecules of swainsonine chloride salts. A crystalline swainsonine bromide salt of the invention may be held together by hydrogen bond interactions from the hydroxyl oxygen atoms of a first molecule of a swainsonine bromide salt to bromide ions of other molecules of swainsonine bromide salts, and a hydrogen bond interaction from the protonated nitrogen atom of the first molecule of a swainsonine bromide salt to an oxygen atom of a second molecule of a swainsonine bromide salt.

Preferably, a crystalline swainsonine hydrochloride salt is provided which comprises molecules of swainsonine hydrochloride salt in a unit cell held together by hydrogen bond interactions from the protonated nitrogen and hydroxyl oxygen atoms of a molecule of swainsonine hydrochloride salt to chloride ions of other molecules of swainsonine hydrochloride salts. In addition, a crystalline swainsonine hydrobromide salt is provided which comprises molecules of swainsonine hydrobromide salt in a unit cell held together by hydrogen bond interactions from the hydroxyl oxygen atoms of a first molecule of swainsonine hydrobromide salt to bromide ions of others molecules of swainsonine hydrobromide salt, and a hydrogen bond interaction from the protonated nitrogen atom of the first molecule to an oxygen atom of a second swainsonine hydrobromide salt molecule.

The crystal may take any crystal symmetry form based on the type of halide salt molecule, the hydrogen bond interactions, and/or the space group. The symmetry form is defined by the "unit cell" which is the basic parallelepiped that repeats in each direction to form the crystal lattice. The term "space group" refers to the arrangement of symmetry elements of a crystal. In an embodiment of the invention, a crystalline swainsonine hydrochloride or hydrobromide salt has space group symmetry $P2_12_12_1$. In a preferred embodiment of the invention, the crystal of the swainsonine chloride or bromide salt comprises orthorhombic unit cells.

The diffraction data obtained from the X-ray crystallography is used to calculate an electron density map of the repeating unit of the crystal. The electron density maps are used to establish the positions of the individual atoms within the unit cell of the crystal. The unit cell axial lengths are represented by (a b c) where a=x axis, b=y axis, and c=z axis. In addition, (x y z) represents the coordinates for each atom measured as the distance along the coordinate axes, a, b, or c, from a point of origin. Those of skill in the art understand that a set of atomic coordinates determined by X-ray crystallography is not without standard error.

The unit cell for a crystal of a swainsonine hydrochloride salt of the invention may have the unit cell lengths a=8.09±0.01 Å, b=9.39±0.01 Å, and c=13.62±0.01 Å. The unit cell for a crystal of a swainsonine hydrobromide salt of the invention may have the unit cell lengths a=8.40±0.01 Å, b=8.63±0.01 Å, c=14.12±0.01 Å. In a preferred embodiment of the invention, the atoms in a crystal of a swainsonine hydrochloride salt have the atomic coordinates as shown in Table 1. In another preferred embodiment of the invention, the atoms in a crystal of a swainsonine hydrobromide salt have the atomic coordinates as shown in Table 2.

The 3-dimensional structures of the hydrochloride and hydrobromide salts of swainsonine expressed using the x, y, and z, coordinates are shown in FIGS. 1 and 2 respectively. Crystal packing diagrams for crystalline hydrochloride and hydrobromide salts of swainsonine are shown in FIGS. 3 and 4, respectively.

Preparation of Swainsonine Salts of the Invention

A crystalline salt of the invention may be prepared by treating swainsonine acetonide with an acid and purifying the salt by crystallization. Swainsonine acetonide can be obtained as described by Bebbett et al and Cha et al (J. Am. Chem. Cos. 111:2580–2582, 1989, and U.S. Pat. No. 5,187,279, respectively). The acetonide can be hydrolyzed to form a substantially pure crystalline salt of the invention. For example, a substantially pure crystalline hydrochloride salt may be formed by hydrolysis of swainsonine acetonide as described in Example 1.

In preparing the compounds of the invention, conventional protecting groups may be used to block reactive groups. Appropriate blocking and deblocking schemes are known to the skilled artisan (See T. W. Greene and P. G. M. Wuts, $2^{nd}$ ed., Protective Groups in Organic Synthesis, John Wiley & Sons, New York, 1991). In general, particular protective groups are selected which adequately protect the reactive groups in question during subsequent synthetic steps and which are readily removable under conditions which will not cause degradation of the desired product. In vivo, some protecting groups are cleaved or metabolically converted into the active functional group (e.g. via hydrolysis or oxidation). Metabolically cleaved protecting groups are preferred, in some cases. Examples of protecting groups that may be used include hydroxyl protecting groups, carboxylate protecting groups, and carbonyl protecting groups.

Representative hydroxyl protecting groups that may be used include the following. Methyl ethers include methoxymethyl; methylthiomethyl, t-butylthiomethyl; (phenyldimethyldiyl)methoxymethyl; benzyloxymethyl; p-methoxybenzyloxymethyl; (4-methoxyphenoxy)methyl; guaiacolmethyl; t-butoxymethyl; 4-pentenyloxymethyl; siloxymethyl; 2-methoxyethoxymethyl; 2,2,2,-trichloroethoxymethyl; bis(2-chlorooxy)methyl; 2-(trimethylsilyl)ethoxymethyl; tetrahydropyran-2-yl; 3-bromotetrahydropyran-2-yl; 1-methoxycyclohexyl; 4-methoxy-tetrahydropyran-2-yl; 4-methoxytetrahydrothiopyran-2-yl; 4-methoxytetrahydrothio-pyran-2-yl-S,S-dioxido; 1-[(2-chloro-4-methyl)phenyl]-methoxypiperidin-4-yl; 1,4-dioxan-2-yl; tetrahydrofuranyl; tetrahydrothiofuranyl; and 2,3,3a,4,5,6,7,7a-octahydro-7,8,8-trimethyl-4,7-methanobenzofuran-2-yl.

Ethyl ethers include 1-ethoxyethyl; 1-(2-chloroethoxy)ethyl; 1-methyl-1-methoxyethyl; 1-methyl-1-benzyloxy-2-fluoroethyl; 2,2,2-trichloroethyl; 2-trimethylsilylethyl; 2-(phenylselenyl)ethyl; t-butyl; allyl; p-chlorophenyl; p-methoxyphenyl; and 2,4-dinitrophenyl.

Benzyl ethers include benzyl; p-methoxybenzyl; 3,4-dimethoxybenzyl; o-nitrobenzyl; p-nitrobenzyl; p-halobenzyl; 2,6-dichlorobenzyl; p-cyanobenzyl; p-phenylbenzyl; 2- and 4-picolyl; 3-methyl-2-picolyl-N-oxido; diphenylmethyl; p,p'-dinitrobenzhydryl; 5-dibenzosuberyl; triphenylmethyl; α-naphthyldiphenylmethyl; p-methoxyphenyldiphenylmethyl; di(p-methoxyphenyl)phenylmethyl; tri(p-methoxyphenyl)methyl; 4-(4'-bromophenacyloxy)phenyldiphenylmethyl; 4,4'4"-tris(4,5-dichlorophthalimidophenyl)methyl; 4,4',4"-tris-(levulinoyloxyphenyl)methyl; 4,4',4"-tris(benzoyloxyphenyl)methyl; 3-(imidazol-1-ylmethyl)bis(4',4"-dimethoxyphenyl)-methyl; 1,1-bis(4-methoxyphenyl)-1'-pyrenylmethyl; 9-anthryl; 9-(9-phenyl)xanthenyl; 9-(9-phenyl-10-oxo)anthryl; 1,3-benzodithiolan-2-yl; and benzisothazolyl S,S-dioxido.

Silyl ethers include trimethylsilyl; triethylsilyl; triisopropylsilyl; dimethylisopropylsilyl; diethylisopropyl-silyl; dimethylthexylsilyl; t-butyldimethylsilyl; t-butyl-diphenylsilyl; tribenzylsilyl; tri-p-xylylsilyl; triphenyl-silyl; diphenylmethylsilyl; and t-butylmethoxyphenylsilyl.

Esters include formate, benzoylformate; acetate; chloroacetate; trichloroacetate; methoxyacetate; triphenylmethoxyacetate; phenoxyacetate; p-chlorophenoxyacetate; p-(phosphate)phenylacetate; 3-phenylproprionate; 4-oxopentanoate (levulinate); 4,4-(ethylenedithio)pentanoate; pivaloate; adamantoate; crotonate; 4-methoxycrotonate; benzoate; p-phenylbenzoate; and 2,4,6-trimethylbenzoate.

Carbonates include methyl carbonate; 9-fluorenylmethylcarbonate; ethyl carbonate; 2,2,2-trichloroethyl carbonate; 2-(trimethylsilyl)ethyl carbonate; 2-(phenylsulfonyl)ethyl carbonate; 2-(triphenylphosphonio)ethyl carbonate; isobutyl carbonate; vinyl carbonate; allyl carbonate; p-nitrophenyl carbonate; benzyl carbonate; p-methoxybenzyl carbonate; 3,4-dimethoxybenzyl carbonate; o-nitrobenzyl carbonate; p-nitrobenzyl carbonate; S-benzyl thiocarbonate; 4-ethoxy-1-naphthyl carbonate; and methyl dithiocarbonate.

Protecting groups with assisted cleavage include 2-iodobenzoate; 4-azidobutyrate; 4-nitro-4-methylpentanoate; 0-(dibromomethyl)benzoate; 2-formylbenzenesulfonate; 2-(methylthiomethoxy)ethyl carbonate; 4-(methylthiomethoxy)butyrate; and 2-(methylthiomethoxymethyl)benzoate.

Miscellaneous esters include 2,6-dichloromethylphenoxyacetate; 2,6-dichloro-4-(1,1,3,3-tetramethylbutyl)phenoxyacetate; 2,4-bis(1,1-dimethylpropyl)-phenoxy-acetate; chlorodiphenylacetate; isobutyrate; monosuOHCinoate; (E)-2-methyl-2-butenoate(tigloate); o-(methoxycarbonyl)benzoate; p-benzoate; α-naphthoate, nitrate; alkyl N,N,N',N',-tetramethylphosphorodiamidate; N-phenylcarbamate; borate; dimethylphosphinothioyl; and 2,4-dinitrophenyl-sulfenate.

Sulfonates include methanesulfonate (mesylate); benzylsulfonate; and tosylate.

Cyclic acetals and ketals include methylene; ethylidene; 1-t-butylethylidene; 1-phenylethylidene; 4(methoxyphenyl) ethylidene; 2,2,2,-trichloroethylidene; acetonide (isopropylidene); cyclopentylidene; cyclohexylidene; cycloheptylidene; benzylidene; p-methoxybenzylidene; 2,4-dimethoxybenzylidene; 3,4-dimethoxybenzylidene; and 2-, 3-, or 4-nitrobenzylidene.

Cyclic ortho esters include methoxymethylene; ethoxymethylene; dimethoxymethylene; 1-methoxyethylidene; 1-ethoxyethylidine; 1,2-dimethoxy-ethylidene; α-methoxybenzylidene; 1-(N,N-dimethylamino)ethylidene derivative; α-(N,N-dimethylamino)benzylidene derivative; and 2-oxacyclopentylidene.

These cyclic ortho esters, like the bivalent organic moities recited above for adjacent pairs of substituents, may react with non-adjacent hydroxyl moieties. For example, a bivalent organic moiety recited in the preceding paragraph or recited above for adjacent pairs of substituents may be selected for two nonadjacent substituents on the same molecule or for any two substitutents on two separate molecules. The two separate molecules can be the same or different, and are selected from compounds disclosed herein.

Silyl derivatives include di-t-butylsilylene groups; 1,3-(1,1,3,3-tetraisopropyldisiloxanylidene) derivative, tetra-t-butoxydisiloxane-1,3-diylidene derivative; cyclic carbonates; cyclic boronates; ethyl boronate; and phenyl boronate.

Preferred protecting groups for catechols include cyclic acetals and ketals such as methylene, acetonide, cyclohexylidene, and diphenylmethylene; and cyclic esters such as cyclic borate and cyclic carbonate.

The invention also encompasses compounds identical to the swainsonine salts of the invention except that one or more conventional protecting groups are used, such as the hydroxyl protecting groups, carboxylate protecting groups, and carbonyl protecting groups described herein.

The invention further encompasses other $C_{1-10}$ hydroxyl protecting groups not individually identified above which are pharmaceutically acceptable, and are optionally metabolized (e.g. cleaved or modified) to form one of the compounds disclosed herein. In other words, the invention, encompasses metabolic precursors of the disclosed compounds and metabolites of the disclosed compounds having anticancer, antiviral, or antiproliferative activity.

Still further, the invention encompasses quaternary amine salts, and other organic salts of the disclosed compounds, including benzenesulfonate, benzoate, citrate, lactate, tartate, preferably formate and acetate, or other carboxylic, aminocarboxylic or polycarboxylic acid salts.

The crystals of the invention may also be formed by for example, dissolving swainsonine hydrochloride or hydrobromide salt in a solvent (e.g. methanol), and evaporating the solvent. The crystals may also be prepared by diffusion using standard methods.

It will also be appreciated that crystalline chloride or bromide salts (particularly hydrochloride or hydrobromide salts) of functional derivatives of swainsonine may be prepared using the methods described herein, and the salts prepared by the methods are contemplated in the present invention. A "functional derivative" of swainsonine refers to a compound that possesses a biological activity (either functional or structural) that is substantially similar to the biological activity of swainsonine. The term "functional derivative" is intended to include "variants" "analogs" or "chemical derivatives" of swainsonine. The term "variant" is meant to refer to a molecule substantially similar in structure and function to swainsonine or a part thereof. A molecule is "substantially similar" to swainsonine if both molecules have substantially similar structures or if both molecules possess similar biological activity. The term "analog" refers to a molecule substantially similar in function to a swainsonine molecule. The term "chemical derivative" describes a molecule that contains additional chemical moieties which are not normally a part of the base molecule.

Compositions of the Invention

The invention provides pharmaceutical compositions formulated from a swainsonine salt of the invention (e.g. a chloride or bromide salt preferably a crystalline hydrochloride or hydrobromide, most preferably an orthorhombic hydrochloride salt of swainsonine), a combination of the swainsonine salts of the invention, or a combination of swainsonine and swainsonine salt(s) of the invention. The compositions include a swainsonine salt of the invention, or include a form of swainsonine prepared from a disclosed salt, such as tablets, capsules including a soft gel capsule, or a powdered or pulverized form of the halide salt or other parenteral, transdermal, intranasal or oral administration forms known to the art.

A preferred composition of the invention is a solid form composition wherein the active ingredient i.e. salt of the invention is in crystalline form. For example, the composition can be in the form of a tablet, capsule, or powder. A particularly preferred solid form composition of the invention having enhanced stability properties comprises a crystalline hydrochloride salt of the invention.

The crystalline salts of the present invention enable the use of a substantially pure active ingredient in pharmaceutical compositions. The term "substantially pure" includes a purity of at least 95%, and preferably at least 97% by weight (e.g. at least 99% to 99.5% by weight). Impurities include by-products of synthesis or degradation. A substantially pure crystalline hydrochloride salt of swainsonine is virtually colorless, and can be in the form of prisms.

A composition of the invention includes one or more pharmaceutical carriers, and optionally one or more bioactive agents. For example, compositions formulated from a salt of swainsonine of the invention may include: (a) a tablet including a swainsonine salt of the invention, a pharmaceutical carrier and may also include an absorption enhancer, (b) a capsule containing a crystalline, amorphous or glassy powder, microspheres, or pellets made from a swainsonine salt of the invention, even though, in the capsule, swainsonine salt is no longer in the form of clear crystals (e.g., prisms), (c) a soft gel capsule made from a swainsonine salt of the invention, (d) an aqueous solution of a swainsonine salt of the invention, wherein the dissolved swainsonine salt is no longer clear crystals, and may for example, no longer be associated with either the hydrogen or the chloride or bromide, and (e) other parenteral, transdermal, intranasal or oral administration forms known to those skilled in the art. Swainsonine free base derived from a salt of the invention is also useful in certain methods of treatment of the invention. Pure swainsonine free base alone, however, is not contemplated for use in a composition of the invention.

Routes of administration include oral, pulmonary, topical, body cavity (e.g., nasal eye, bucal), transdermal, and parenteral (e.g. intravenous, intramuscular, and subcutaneous routes). Externally activated drug delivery systems include those activated by heat, ultrasound, electrical pulse, iontophoresis, electrophoresis, magnetic modulation, and light.

Formulations include solids (tablets, soft or hard gelatin capsules), semi-solids (gels, creams), or liquids (solutions, colloids, or emulsions), preferably solids. Colloidal carrier systems include microcapsules, emulsions, microspheres, multi-lamellar vesicles, nanocapsules, uni-lamellar vesicles, nanoparticles, microemulsions, and low-density lipoproteins. Formulation systems for parenteral administration include lipid emulsions, liposomes, mixed micellar systems, biodegradable fibers, and fibrin-gels, and biodegradable polymers for implantation. Formulation systems for pulmonary administration include metered dose inhalers, powder inhalers, solutions for inhalation, and liposomes. A composition can be formulated for sustained release (multiple unit disintegrating particles or beads, single unit non-disintegrating system), controlled release (oral osmotic pump), and bioadhesives or liposomes. Controlled release formulations include those, which release intermittently, and those that release continuously.

Pharmaceutical carriers include inorganics such as calcium phosphate and titanium dioxide; carbohydrates such as -lactose monohydrate and -cyclodextrin; surfactants such as sodium lauryl sulfate and poloxamers; polymers such as starch, ethyl cellulose, hydrogels, and polyacrylic acids; lipids such as polylactides, stearic acid, glycerides, and phospholipids; or amino acids and peptides such as leucine and low density lipoprotein.

The composition is formulated so that it remains active at physiologic pH. The composition may be formulated in the pH range 4 to 7.

In an embodiment of the invention a composition is provided which is an oral dosage form comprising a swainsonine salt of the invention (preferably the crystalline hydrochloride or hydrobromide salt) and a non-hygroscopic, inert and preferably anhydrous excipient (e.g. lactose or mannitol). In another embodiment, a composition is provided which is a soft gelatin capsule comprising a swainsonine salt of the invention (preferably a crystalline hydrochloride or hydrobromide salt) and at least one hydrophilic vehicle ( e.g. glycerin or propylene glycol) and at least one lipophilic vehicle (e.g. PEG 400).

Compositions can also include absorption enhancers, particle coatings (e.g. enteric coatings), lubricants, targeting agents, and any other agents known to one skilled in the art. A composition may contain from about 0.1 to 90% by weight (such as about 0.1 to 20% or about 0.5 to 10%) of the active ingredient. The percentage of active ingredient in each pharmaceutical composition and the effective amount of the active ingredient used to practice the present invention for treatment of the disclosed conditions depend upon the manner of administration, the age and the body weight of the subject and the condition of the subject to be treated, and ultimately will be decided by the attending physician or veterinarian. Such amount of the compound as determined by the attending physician or veterinarian is referred to herein as the "effective amount". Based on studies by Goss et al, (1994, and 1996) with swainsonine free base a dose of less than 300 $\mu$g/kg/day, preferably 150 $\mu$g/kg/day, or less, most preferably a dose of 75 $\mu$g/kg twice daily, or less, will be well tolerated in humans.

The salts of the invention are indicated as therapeutic agents either alone or in conjunction with other therapeutic agents or other forms of treatment (e.g. chemotherapy or radiotherapy). For example, the compounds may be used in combination with anti-proliferative agents, antimicrobial agents, immunostimulatory agents, or anti-inflammatories. In particular, the compounds may be used in combination with and may enhance the activity of anti-viral and/or anti-proliferative agents such as a Th1 cytokine. Th1 cytokines include interleukins-2 and 12 (IL-2, IL-12), and the interferons-$\alpha$, $\beta$, $\gamma$ (IFN-$\alpha$, IFN-$\beta$, IFN-$\gamma$), and inducers thereof. The compounds of the invention can be used with poly (I.C.), poly (I.C.) LC, tumor necrosis factor (TNF), or transforming growth factor (TGF). The compounds can be M used in combination with chemotherapeutic agents including doxorubicin, 5-fluorouracil, cyclophosphamide, and methotrexate, with isoniazid for the prevention and treatment of peripheral neuropathy, and with NSAID for the prevention and treatment of gastroduodenal ulcers. The compounds of the invention may be administered concurrently, separately, or sequentially with other therapeutic agents or therapies.

Subjects which may be administered a composition of the invention include animals, including mammals, and particularly humans. Animals also include domestic animals bred for food or as pets, including horses, cows, sheep, poultry, fish, pigs, cats, dogs, and zoo animals.

The swainsonine salts of the invention may be converted into pharmaceutical compositions using customary methods. For example, a crystalline swainsonine hydrochloride or hydrobromide salt of the invention may be mixed into a selected pharmaceutically acceptable carrier, excipient, or diluent as described herein.

Mannosidase Inhibition

The compounds of the invention, in particular, crystalline swainsonine hydrochloride and hydrobromide salts and compositions made therefrom inhibit the enzyme Golgi mannosidase II. General mannosidase inhibition of the compounds of the invention can be confirmed by directly measuring inhibition of Jack Bean, Golgi, or lysosomal $\alpha$-mannosidase (See Example 18 for protocols). Mannosidase inhibition may also be tested using an L-PHA toxicity assay. The assay is based on the finding that the specific binding of the toxic plant lectin L-PHA to transformed cell lines such as MDAY-D2 tumor cells is a specific measure of inhibition of oligosaccharide processing. The measurement of $IC_{50}$ in the L-PHA toxicity assay reflects the ability of the compound to enter into cells and to effect inhibition of oligosaccharide processing. It is a general screen for activity in cells which measures cell entry, inhibition of the target enzyme, and the resulting cellular phenotype.

The L-PHA assay generally involves growing transformed cells in the presence of L-PHA and the compound; measuring cell viability and/or the amount of proliferation of the cells; and determining the ability of the compound to inhibit N-linked oligosaccharide processing by comparing the amount of proliferation of the cells and/or cell viability with the amount of proliferation observed for the cells grown in the presence of L-PHA alone. Transformed cells which may be used in this assay include MDAY-D2, L1210, CHO, B16, melanoma tumor cells, and human tumor cells such as SW 480, LS174T, HT-29, WiDr, T2, MDA-231, MCF7, BT-20, Hs578T, K562, Hs578T, SK-BR-3, CY 6T, MDA-468, H23, H157, H358, H1334, H1155, H28, H460, Hmesol, H187, H510A, N417, H146, H1092, H82 (Restifo, N. P. et al, J. Exper. Med. 177:265–272, 1993).

The amount of proliferation of the cells may be measured using conventional techniques. For example, cell proliferation may be measured by measuring incorporation of labeled thymidine. More particularly, radioactively labeled thymidine may be added for about 2–5 hours, preferably 3–4 hours and the cells can be harvested and radioactivity counted using a scintillation counter.

A fully automated enzymatic method based on measurement of alkaline phosphatase activity may be used to screen for inhibition of mannosidase II. The method is based on the observation that the number of surviving cells and their level of alkaline phosphatase activity are closely correlated. The method employs a colorimetric assay to monitor cell proliferation of transformed cells after L-PHA treatment. The reaction mixture is directly added to cells growing in their own medium, as cell pelletting and washing steps are not required. Thus, the method can be carried out in a single step, without removal of the culture medium or cell pelletting and washing, thereby permitting the fully automated procedures. The reaction is linear with time in a wide time interval (5–180 min), and the $K_m$ value of the enzyme for the substrate para-nitrophenylphosphate is relatively low (0.81 mM). Incubation time and substrate concentration can be changed in order to modulate the velocity of the reaction and adjust the protocol, for automation and timing purposes, to the number of samples. Use of a robotic platform also allows simultaneous processing f large numbers of samples, e.g. thirty-six 96well plates.

The automated method typically comprises (a) reacting a compound of the invention with a transformed cell in the presence of L-PHA, and measuring alkaline phosphatase activity; and (b) comparing to a control in the absence of the compound wherein an increase in alkaline phosphatase activity indicates that the compound has the ability to inhibit N-linked oligosaccharide processing. Transformed cells which may be used in the method of the invention include the cell lines described herein or cell lines that contain either constitutive or inducible enzyme activity such as osteoblastic cell lines. An alkaline phosphatase expression construct can be introduced in the cells to amplify the signal. The amount of proliferation of the cells is measured by measuring alkaline phosphatase activity. Alkaline phosphatase may be measured using conventional methods for example by using para-nitrophenylphosphate as a substrate and measuring absorbance at 405 nm.

The conditions for carrying out the method will be selected having regard to the nature of the compound and the cells employed. For example, if the transformed cells are MDAY-D2 tumor cells a concentration of about $1–6 \times 10^3$ cells, preferably $5 \times 10^3$ may be used. The MDAY-D2 cells are generally cultured for about 10 to 30 hours, preferably 16 to 20 hours, followed by addition of L-PHA at a concentration of about 50 to 150 $\mu$g/ml, preferably 100 $\mu$g/ml. The alkaline phosphatase assay mixture may contain a buffer e.g. diethanolamine buffer, and para-nitrophenylphosphate at a concentration of about 1.5 to 4 mM, preferably 2 to 3 mM, most preferably 2.5 mM.

The automated method of the invention may generally be used to identify compounds that antagonize inhibitors of cell proliferation. For example, the method may be used to identify antagonists of cell growth inhibitors such as TGFβ or apoptotic agents such as TNFα. Therefore, the invention broadly contemplates a method comprising (a) reacting a test compound with a transformed cell in the presence of a cell growth inhibitor; (b) measuring alkaline phosphatase activity; and (c) comparing to a control in the absence of the test compound wherein an increase in alkaline phosphatase activity indicates that the compound has the ability to antagonize the cell growth inhibitor.

Properties of the Swainsonine Salts of the Invention

The salts of the invention have valuable pharmacological properties and they provide antimicrobial, cancer suppressing effects, hemorestorative, chemoprotective, radioprotective, and immunomodulatory properties, and in particular, they may stimulate the Th1 arm of the cellular immune response. These properties are discussed in more detail below.

Cancer Suppressing Properties

Blocking of the carbohydrate processing enzyme Golgi α-mannosidase II, prevents normal maturation of N-linked oligosaccharides into "complex-type" structures (Elbein, A. D. *Ann. Rev. Biochem.* 56:497–534, 1987) which are known to be important for growth and metastatic spread of tumor cells (Dennis, J. W *Science* 236:582–585, 1987). In animal and tumor models, treatment with a Golgi mannosidase II inhibitor has been shown to inhibit the rate of tumor growth and metastasis (Dennis *Cancer Res.* 46:5131–5136, 1986. 1. Dennis, J. W., *Cancer Res.* 50:1867–1872, 1990. Newton, S. A., *J.Natl. Cancer Inst.* 81:1024–1028, 1989). Golgi mannosidase II inhibitors such as swainsonine have cancer suppressing properties in a wide variety of tumor types including direct anti-metastatic and anti-invasion effects on tumor cells, and other anti-cancer activities such as immune stimulatory effects and myeloproliferative and hemorestorative activities as described herein.

Immune Stimulatory Properties

Blocking the pathway at Golgi α-mannosidase II causes an accumulation of "hybrid-type" carbohydrate structures, which have terminal mannose residues. The exposed mannose residues are an important feature directly related to immune stimulation (Sherblom, A. P et al. *J. Immunol.* 143:939–944, 1989; Yagita, M. and Saksela, *Scand. J. Immunol.* 31:275–282, 1990). At the molecular level, it has been shown that certain cytokines, including interferon (IFN), interleukin-2 (IL-2) and tissue necrosis factor (TNF-α), bind to carbohydrate structures terminating in mannose structures such as those which accumulate when Golgi mannosidase II is blocked. These carbohydrate structures are found on the cell surface, and are suggested to enhance cytokine binding to cell surface glycoproteins and receptors or co-receptors that are required to transmit the cytokine's action into a cellular immune response.

Following infection with viral, bacterial, or fungal pathogens, the host immune response involves inflammation and activation of cellular and humoral arms of the immune system. CD4$^+$T cells can be stimulated to differentiate into helper T cells with the Th1 phenotype which is associated with cellular immunity, or Th2 phenotype which is associated with antibody production (Shindler, Annu Rev. Biochem 64:621–651, 1995). TH1 cells are characterized by production of the cytokines INF-α, IL-2, TNFα, IL-12 while the Th2 cells produce the cytokines IL-4 and IL-10. Th1 cytokines further promote the Th1 response, while suppressing the Th2 response and conversely, Th2 cytokines promote the Th2 response and suppress the Th1 response. The balance between the Th1 and Th2 responses is a major determinant of the outcome of infectious diseases, as well as autoimmunity and allergic reactions.

Inhibition of Golgi α-mannosidase in mice and cell culture has been shown to enhance the Th1-dependent cell mediated immune responses. This includes activation of natural killer (NK) and lymphokine activated killer (LAK) cells as well as T cell stimulation by antigens and IL-2 (Wall, K. A., Proc, Natl. Acad, Sci. USA 85:5644–5648, 1988). Inhibition of Golgi α-mannosidase also enhances tissue necrosis factor (TNFα)-dependent stimulation of macrophage (Muchmore et al., Cancer res. 50: 6285–6290, 1990) and Il-2 dependent stimulation of LAK cells in vitro (Yagita et al., Scand. J. Immunol. 31:275–282, 1990). In addition, inhibition of Golgi α-mannosidase enhances the response to α-IFN, including the anti-tumor and anti-proliferative responses, as well as the induction of 2'–5' oligoadenylate synthetase and TIMP (Tissue Inhibitors of Metalloproteases) gene expression (Dennis, JNCI 81:1028–1033, 1989, Korczak et al., Int. J. Cancer 53:634–639, 1993).

Cytokines bind to cell surface receptors and transmit signals to the nucleus via phosphorylation and dimerization of the Signal Tranducers and Activators of Transcription (STAT) family of transcription factors. STAT1 is required for the anti-viral response to α-IFN, for the Th1 immune response and associated cytokine production, and for the clearance of the mouse hepatitis virus in vivo (Durbin et al, Cell 84:443–450, 1996). Evidence for this is provided by the null mutant STAT1 mouse, which is developmentally normal, is highly sensitive to viral hepatitis infection and unresponsive to IFN (Meraz, M. A et al. Cell 84:431–442, 1996). STAT3 activation is associated with inflammation, notably the IL6 dependent response. STAT6 is required for the Th2 response, as null mutant mice are deficient in Th-2 (antibody-dependent) immune responses and lack the normal IgG response to nematode infection. STAT4 is also required for the Th1 response as mice deficient in this gene show a defect in IL-12 dependent stimulation of NK and LAK cells, as well as in the production of Th1 cytokines (Kaplan, Nature 382: 174–177, 1996).

The Th1 cellular immune response has been shown to be essential for the suppression of tumor growth and metastasis, and the elimination of certain viral, bacterial, fungal and parasitic infections, and cancer. The importance of the Th1 response has been demonstrated for chronic viral infections including hepatitis B (Milich D R. Schodel F. Hughes J L. Jones J E, Peterson D L. 1997. *J Virol* 71:3:2192–2201), hepatitis C (Tsai S L, Liaw Y F, Chen M H, Huang C Y, Kuo G C 1997. *Hepatology* 25:2:449–458), HIV (Clerici M, Shearer G M. 1994. Immunol Today 15:12:575–581), herpes simplex labialis (Spruance S L, Evans T G, McKeough M B, Thai I, Araneo B A, Daynes R A, Mishkin E M, Abramovitz A S. 1995. *Antiviral Res* 28:1:39–55), bacterial infections such as *Pseudomonas aeruginosa* infection of the respiratory tract in a rat model of cystic fibrosis (Johansen H K 1996. *APMIS Suppl* 63:5–42), leprosy caused by *Mycobacterium leprae* (Modlin R L 1994; *J Invest Dermatol* 102:6:828–832), fungal infections including *Candida albicans* (Romani L, et al., 1995;*Immunol Res* 14:2:148–162) and parasitic infections including Leishmania (Kemp M, 1997. *APMIS Suppl* 68, 1–33), and schistosomiasis, caused by one of the five species of the flatworm known as schistosomes (Wynn T A et al., 1996. *J Immunol* 157:9: 4068–4078.).

While interferon and interferon-inducers have anti-cancer and anti-viral activity, they appear to be insufficient alone in stimulating an appropriate Th1 response capable of eliminating disease. For example, interferons have been used in clinical trials for the treatment of most types of cancer, with variable efficacy (Goldstein D and Lasglo J, *Can Res* 46:4315, 1986). Interferons have also been shown to have some efficacy in the treatment of hepatitis C and hepatitis B. In hepatitis, an initial response to α-IFN occurs in less than 50% of patients, and in hepatitis C, 75–90% of all α-IFN treated patients relapse (Hoofnagle J H, et al. 1986 *New Engl J Med;*315:1575–1578; Davis G L et al. 1989 *New Engl J Med;* 321:1501–1506). In addition, another Th1 cytokine, IL-2 has been shown to have efficacy in the treatment of some cancers, in patients with HIV and in leprosy (*Curr Opin Biotech* 4:6: 722–726, 1993).

Hemorestorative Properties/Protection Against Lethality of Radiation and Chemotherapy Myelosuppression is often the dose-limiting feature in chemotherapy for a number of diseases including cancer (Hoagland, Hematologic Complications of Cancer Chemotherapy. In: *The chemotherapy source book*, Perry M C (ed) pp. 498–507, Williams & Wilkins: Baltimore 1992) and acquired immune deficiency syndrome (AIDS) (McLeod and Hammer, Ann. Int. Med 117: 487, 1992; Richman et al, N Eng J Med 317:192, 1987; Shaunak and Bartlett, Lancet II:91, 1989; Walker et al, Clin Res 35:435A, 1987). Supporting patients through periods of myelosuppression or decreased resistance to infection is a critical part of chemotheapeutic regimens. Inhibitors of Golgi mannosidase II (for example swainsonine free base) have been shown to protect against the lethality of various chemotherapeutic agents (Oredipe et al, 1991) as well as against lethal doses of irradiation (White et al, Cancer Comm 3:83–90, 1991). In these studies, enhanced survival in the swainsonine-treated mice correlated with stimulation of bone marrow proliferation, bone marrow cellularity and engraftment efficiency in the mice (Oredipe et al, 1991; White et al, 1991) as well as improvement in peripheral blood counts.

Treatments Using the Swainsonine Salts of the Invention

It is apparent that the salts of the invention can be used in a method for the prevention, treatment and prophylaxis of tumor growth and metastasis of tumors. The salts and compositions of the invention are especially useful in methods for the treatment of various forms of neoplasia such as leukemias, lymphomas, melanomas, adenomas, sarcomas, and carcinomas of solid tissues in patients. In particular, the salts and compositions can be used for treating malignant melanoma, pancreatic cancer, cervico-uterine cancer, ovarian cancer, cancer of the kidney such as metastatic renal cell carcinoma, stomach, lung, rectum, breast, bowel, gastric, liver, thyroid, head and neck cancers such as unresectable head and neck cancers, lymphangitis carcinamatosis, cancers of the cervix, breast, salivary gland, leg, tongue, lip, bile duct, pelvis, mediastinum, urethra, bronchogenic, bladder, esophagus and colon, non-small cell lung cancer, and Kaposi's Sarcoma which is a form of cancer associated with HIV-infected patients with Acquired Immune Deficiency Syndrome (AIDS).

The salts and compositions of the present invention can be used to treat immunocompromised subjects. For example, they can be used in a subject infected with HIV, or other viruses or infectious agents including bacteria, fungi, and parasites, in a subject undergoing bone marrow transplants, and in subjects with chemical or tumor-induced immune suppression.

The salts and compositions of the invention can be used as hemorestorative agents and in particular to stimulate bone marrow cell proliferation, in particular following chemotherapy or radiotherapy. The myeloproliferative activity of salts and compositions of the invention may be determined by injecting the compound into mice, sacrificing the mice, removing bone marrow cells and measuring the ability of the compound to stimulate bone marrow proliferation by directly counting bone marrow cells and by measuring clonogenic progenitor cells in methylcellulose assays.

The salts and compositions of the invention also can be used as antiviral agents in particular on membrane enveloped viruses such as retroviruses, influenza viruses, cytomegaloviruses and herpes viruses. The salts and compositions of the invention can also be used to treat bacterial, fungal, and parasitic infections.

The compounds of the invention can also be used in the treatment of inflammatory diseases such as rheumatoid arthritis and asthma. The compounds inhibit mannosidase and may render carbohydrate structures on neutrophils unable to bind to selecting. Selectins present at the site of damage interact with the carbohydrate structures on neutrophils in such a way that the neutrophils roll along the epithelial wall, stick, infiltrate, and cause tissue damage.

The salts of the invention have particular application in the prevention of tumor recurrence after surgery i.e. as an adjuvant therapy.

It is evident from the properties of the salts of the invention that they may also be used to augment the anti-cancer effects of agents such as interleukin-2 and poly-IC, to augment natural killer and macrophage tumoricidal activity, induce cytokine synthesis and secretion, enhance expression of LAK and HLA class 1 specific antigens, activate protein kinase C, stimulate bone marrow cell proliferation including hematopoietic progenitor cell proliferation, and increase engraftment efficiency and colony-forming unit activity, to confer protection against chemotherapy and radiation therapy (e.g. chemoprotective and radioprotective agents), and to accelerate recovery of bone marrow cellularity particularly when used in combination with chemical agents commonly used in the treatment of human diseases including cancer and acquired immune deficiency syndrome (AIDS). For example, the salts of the invention may be used as chemoprotectants in combination with anti-cancer agents including doxorubicin, 5-fluorouracil, cyclophosphamide, and methotrexate, and in combination with isoniazid or NSAID.

The activity of the salts of the invention for a particular treatment application may be tested in various in vitro and in vivo models described herein and known in the art. In particular, anti-metastatic effects of the salts and compositions of the invention may be demonstrated using a lung colonization assay. For example, melanoma cells treated with a compound may be injected into mice and the ability of the melanoma cells to colonize the lungs of the mice may be examined by counting tumor nodules on the lung after death. Suppression of tumor growth in mice by the compound administered orally or intravenously may be examined by measuring tumor volume. Cellular models and animal models that confirm the anti-cancer effects of the salts of the invention include the models set out in Table 3. Examples of protocols for confirming the activities of the salts of the invention are included in the Example section.

Other embodiments of the invention provide a method of treating a disclosed condition which includes exposing a subject in need of such exposure to a pharmaceutically effective amount of a swainsonine salt of the invention, a metabolite of a disclosed swainsonine salt, or a prodrug or metabolic precursor of a metabolite thereof. In this embodiment, the metabolite may be used as an agent for example against a hepatitis C infection.

A salt or composition of the invention may be used as a vaccine adjuvant to induce a potent immune response to itself and/or induce immunity to antigens, particularly antigens that are normally poor immunogens. The salt or composition of the invention may augment vaccine immunogenicity through activation of antigen presenting cells, such as monocytes or macrophages, to release cytokines that can promote T-cell help for B cell and CTL response. As a result, the salt or composition may induce a more favorable antibody response with high titers, which appear earlier in the course of immunization and persist over time, as well as increase memory responses and CD8+ MHC Class I-restricted CTL. A salt or composition of the invention may be contained in a vaccine or it may be administered separately. A salt of the invention may be used to enhance immunogenicity of antigens that induce T cell responses (e.g. T cell antigens), and in particular they may be used to enhance the immunogenicity of carbohydrate antigens associated with cancers or infectious diseases. Examples of vaccines which may employ a salt or composition of the invention to augment immunogenicity include cancer vaccines (e.g. breast cancer vaccines), and vaccines for chronic infectious diseases.

EXAMPLES

Example 1

Synthesis of Swainsonine Hydrochloride

Swainsonine free base (203.7 mg, 1.18 mmol) was dissolved in 4.0 ml distilled water. Aqueous 1 M hydrocholoric acid (1.41 ml, 1.2 equiv) was added. After freeze drying, the amorphous residue was crystallized from methanol-ether or ethanol.

Swainsonine hydrochloride (448.6 mg) was dissolved in 5.0 ml methanol. After filtering, about 6.3 ml diethyl ether was added dropwise over a time interval of 30 minutes with occasional swirling of the solution. Crystals began to form after 0.25 ml of ether were added. The crystallizing solution was left at room temperature for 20 minutes. After filtering by suction and washing with 6 ml of 1:2:methanol:diethyl ether, colorless crystals were obtained (347.1 mg, 77.4% yield). This synthesis does not require chromatographic purification.

The melting point of the clear swainsonine hydrochloride crystal (prism) was 190–191° C. The solubility of swainsonine hydrochloride in distilled water at room temperature was about 3 g/ml, in contrast to the solubility of swainsonine free base, which is about 0.8 g/ml (see Table 5).

Example 2

Synthesis of Swainsonine Hydrochloride

Swainsonine hydrochloride can be synthesized from 1,2-O-isopropylidene swainsonine. A 10% (w/v) solution of 1,2-o-isopropylidene swainsonine in tetrahydrofuran, methanol ethanol, or isopropanol is acidified by adding the same volume of aqueous 6M hydrochloric acid. After stirring overnight at ambient temperature the solution is concentrated to dryness. The residue is dissolved in methanol or ethanol and decolorized with charcoal (50° C. m 15 min). The charcoal is filtered off and the residue crystallized as described in Example 1.

Example 3

Stability of Swainsonine Hydrochloride

Samples of swainsonine free base synthesized using synthetic routes developed by Dr. David Dime (Toronto Research Chemicals, Toronto, Ontario) and Dr. William Pearson (University of Michigan, Ann Arbor, Mich.), were recrystallized to obtain either the hydrochloride salt, the hydrobromide salt or the free base of swainsonine. Samples were weighed and exposed to the conditions described below.

To model long-term stability or shelf life, various conditions were used to accelerate the decomposition process. Samples of crystalline prism swainsonine hydrochloride salt and swainsonine free base (a white, fluffy powder obtained from swainsonine hydrochloride were recrystallized from chloroform-methanol-diethyl ether) were weighed and exposed to conditions described below (stressed samples). Unstressed samples were prepared at 1 mg/ml concentration and chromatographed in sextuplicate on each run. After the indicated time interval each stressed sample was diluted with mobile phase at the same concentration as the unstressed sample. The percentage remaining swainsonine hydrochloride or swainsonine free base was calculated based on the percentage of either the hydrochloride or the free base in the unstressed sample.

The conditions included (a) UV light for 7 days; (b) 105° C. with atmospheric oxygen for seven days (*=average of two samples); (c) 105° C. under nitrogen for seven days (*=average of two samples); (d) 70° C. with low humidity for seven days; and (e) 40° C. with 75% relative humidity for seven days. Other tests include (f) UV for 24 hours; (g) 100° C. aqueous solution for two hours; (h) aqueous acidic treatment for 24 hours; (i) aqueous alkali treatment for 4 hours; and (j) (aqueous) 3% hydrogen peroxide for 4 hours. Surprisingly, the thermal stability of the hydrochloride salt is greater than that of the free base or the hydrobromide salt (see Table 4). Furthermore, the photochemical stability of the hydrochloride salt is significantly greater than that of the hydrobromide salt (see Table 4). The physical properties of swainsonine hydrochloride compared to the free base and swainsonine hydrobromide, and swainsonine hydrofluoride are shown in Table 5.

Swainsonine hydrochloride, hydrobromide and free base were exposed to 50° C./50% relative humidity (RH) and 80° C./ambient humidity for 4 weeks. At baseline, and at intervals of 1 week, the stability of test materials is measured by HPLC as above. In addition, colour and moisture evaluation is performed at the beginning and end of the study, and samples of the base and salts are weighed, and the colour and formation of water are also noted.

Example 4

Synthesis of Swainsonine Hydrobromide

Swainsonine free base (299.7 mg) was dissolved in distilled water (6.5 ml). Aqueous 1 M hydrobromic acid (1.1 equiv) was added and the solution was freeze-dried. The residue was crystallized from methanol-diethyl ether in a manner similar to that of the hydrochloride salt in Example 1. Swainsonine hydrobromide salt (341 mg, 77.6%) was obtained as colorless crystals with melting point of 153–154° C.

Example 5

Synthesis of Swainsonine Hydrogen Fluoride

Swainsonine free base (301.03 mg) was dissolved in methanol (10 ml) and aqueous 48% hydrogen fluoride solution (84 microliters) was added. After concentrating the solution, the residue was crystallized from boiling methanol. Colorless needles (14.9 mg, 4.5%) were obtained. These needles decompose above 152° C. without melting.

Example 6

X-ray Crystallographic Analysis of Swainsonine Hydrochloride and Swainsonine Hydrobromide X-ray crystallographic analysis was carried out using conventional procedures. Space groups and cell parameters were determined from precession camera photographs. Refined cell parameters were obtained by diffractometer measurements of 12 high angle reflections ($40° < 2\theta < 60°$) and application of the least squares method. Crystallographic data are given in Tables 1 and 2. Crystal dimensions were chosen for data collection on a diffractometer, using copper $K\alpha$ radiation and a $\theta 2\theta$ scan mode with a scan speed of 2°/min. Three standard reflections, monitored every 100 reflections, showed only random intensity variations within 5%. The intensities were corrected for Lorentz and polarization factors. No absorption corrections were applied. The crystal structures were determined by direct methods using a program such as the SHELXS-86 program or SIR-88 program. In each case the E-map revealed the positions of all non-hydrogen atoms in the structures. Structure refinement and difference electron density calculations revealed no residual electron density. The final discrepancy factors converged at R=3.6% at $2\sigma$ for ≈1200 intensity data (hydrochloride salt) and R=3.8% at $2\sigma$ for 1002 intensity data (hydrobromide salt).

The 3-dimensional structure of swainsonine hydrochloride salt is shown in FIG. 1, while the structure of swainsonine hydrobromide salt is shown in FIG. 2. FIGS. 3 and 4 are crystal packing diagrams for swainsonine hydrochloride and swainsonine hydrobromide, respectively.

The unit cell lengths for the hydrochloride salt are a=8.086±0.01, b=9.386±0.01, c=13.621±0.01 Å. The unit cell is orthorhombic (all angles=90°) and the space group is $P2_12_12_1$. The atomic coordinates for the salt are shown in Table 1. The final discrepancy factor R=3.6% at $2\sigma$ for about 1200 intensity data. Some torsion angles are as follows: H7-C7-C8-H8 39.75±3.33; H8-C8-C9-$H9_1$ −140.68°±3.10; H8-C8-C9-$H9_2$ −20.90°±2.86. The best least square planes of the SW hydrochloride salt and SW diacetate are set out in Table 6. From Table 6 it is apparent that the 4 atoms in swainsonine diacetate are marginally flatter than in swainsonine hydrochloride crystal structure. The molecules of swainsonine hydrochloride in the unit cell are held together by hydrogen bond interactions between the protonated N atom and three hydroxyl oxygen atoms of one molecule to the chloride ions of other molecules. The bond distances are as follows: N1-H1=0.88 Å, from H1 to the chloride ion 2.35 Å; O5-H50=0.78; from H50 to the chloride ion 2.33 Å; O7-H70=0.74 Å; from H70 to the chloride ion 2.44 Å: O8 to H80=0.67 Å; and, from H80 to the chloride ion 2.50 Å.

The unit cell lengths for the hydrobromide salt are a=8.405±0.01, b=8.629±0.01, c=14.118±0.01Å. The unit cell is orthorhombic (all angles=90°), and the space group is $P2_12_12_1$. The atomic coordinates for the salt are shown in Table 2. The final discrepancy factor R=3.8% at $2\sigma$ for about 1200 intensity data. Some torsion angles are as follows: H7-C7-C8-H8 40.07±0.21; H8-C8-C9-$H9_1$ −137.29°±0.09; H8-C8-C9-$H9_2$ −16.96°±0.19. The best least square planes of the SW hydrochloride salt diacetate are set out in Table 6. The molecules of swainsonine hydrobromide in the unit cell are held together by hydrogen bond interactions between the three hydroxyl oxygen atoms of a first molecule to the bromide ions of other molecules, and the protonated N atom of the first molecule to an oxygen atom on a second molecule. The bond distances are as follows: N1-H=0.91 Å; from H to the oxygen atom O8 1.94 Å; O5-H50=0.82 Å; from H50 to the bromide ion 2.47 Å; O7-H70=0.82 Å; from H70 to the bromide ion 2.61 Å; O8 to H=0.82 Å; and, from H to the bromide ion 2.56 Å.

The main significant difference between the crystal structures of the hydrochloride and hydrobromide salts is in the intermolecular hydrogen bonding scheme. In swainsonine hydrochloride, each $Cl^-$ ion is the acceptor for 4 hydrogen bonds; from N—H . . . Cl; O5-H . . . Cl; O8-H . . . Cl. In swainsonine hydrobromide, the $Br^-$ ion occupies a different position with respect to the swainsonine molecule and is an acceptor for 3 H-bonds, from O5-H . . . Br; O7-H . . . Br; O8-H . . . Br and the nitrogen-H bond is to an O8, i.e. N—H . . . O8.

Example 7

NMR Spectra of Swainsonine and Swainsonine Hydrochloride

The $^1$H and $^{13}$C NMR spectra of samples of swainsonine and swainsonine hydrochloride were analyzed by comparison with data reported for swainsonine (M. J. Schneider, et al., Tetrahedron 39:29, 1983). The compounds used in the study were dissolved in D$_2$O (Isotec, Inc.) to a concentration of approximately 4.5 mg/mL. The $^1$H chemical shifts reported in Table 7 were confirmed by COSY and $^1$H-$^{13}$C HSQC experiments. The differentiation of axial and equatorial protons in the six-membered ring was achieved by examination of the vicinal coupling constants and the general observation that axial protons in six-membered rings are usually shielded relative to the equatorial protons (F. A. Bovey. Nuclear Magnetic Resonance Spectroscopy. Academic Press, New York 1988). The methylene protons at C-3 on the five-membered ring were assigned to pseudo-axial and pseudo-equatorial positions by the 2-D ROSEY experiment (provides data similar to a 2-D NOE spectrum but creates the through space correlations between protons by a rotating frame NOE mechanism A. Bax and D. G. Davies, J. Magn. Reson. 63: 207, 1985; D. Heuhaus and M. Williamson. The Nuclear Overhauser Effect in Structural and Conformational Analysis. VCH Publishers Inc., New York. 1989; and W. E. Hull in Two-Dimensional NMR Spectroscopy-Applications for Chemists and Biochemists. $2^{nd}$ Edition. Edited by W. R. Croasmun and R. M. K. Carlson. VCH Publishers Inc. New York. 1994. Ch.2). The C-3 methylene protons (2.754 and 2.420 ppm) appeared as the AB part of an ABX spin system with H-2 (4.217 ppm). This assignment was also supported by the larger vicinal coupling constant with H-2 of 7.9 Hz since the dihedral may be less than 60° between H-2 and H-3. Coupling constants are reported for only those multiplets which displayed well resolved splitting. The equatorial protons of the six-membered ring appeared as unresolved broadened multiplets owing to the superposition of several small coupling interactions.

The $^{13}$C chemical shifts (Table 9) were confirmed by the J-modulated spin sort and $^1$H-$^{13}$C HSQC spectra. When substituent effects in the-six-membered ring were taken into account the chemical shifts for C-5 and C-6 were in accord with the model compound perhydroindolizine (H. O. Kalinowski, S. Berger and S. Braun, Carbon-13 NMR Spectroscopy. J. Wiley and Sons, New York. 1988).

The same procedures were used to assign the NMR spectra of swainsonine hydrochloride. An initial examination of the $^1$H NMR spectrum indicated a deshielding of all the chemical shifts relative to sample SW (Table 7). Protons on C-3, C-5, and C-9 were the most affected by the nitrogen protonation. Most of the chemical shift assignments for swainsonine hydrochloride (SWHCl) could be made by comparison with the SW data, however, COSY and ROESY spectra were required to confirm the assignments particularly of the C-3 protons. In sample SWHCl there was a reversal of the order of the chemical shifts of the pseudo-axial and pseudo-equatorial C-3 protons. The pseudo-axial C-3 proton was at higher frequency in SWHCl (3.379 ppm) relative to the pseudo-equatorial C-3 proton (3.306 ppm). This assignment was confirmed by the ROESY data where the 3.379 ppm multiplet displayed clearly resolved through space correlations with the axial protons at C-9 (2.959 ppm) and C-5 (2.805 ppm). The vicinal coupling constants between the C-3 protons and H-2 support these assignments (Table 8).

The carbon chemical shifts were assigned from the J-modulated spin sort and $^1$H-$^{13}$C HSQC spectra. With the exception of C-5 all the carbon resonances of SWHCl were shielded by varying amounts relative to SW (Table 9). This is generally observed when alkylamines undergo protonation (H. O. Kalinowski, 1988, supra). The shielding experienced by the six-membered ring carbons 6 and 8 may also be attributed in a small part to the introduction of an axial hydrogen on the nitrogen. The axial N—H would create 1,3-diaxial steric interactions with the C-6 and C-8 axial protons resulting in the γ-substituent effect on the C-6 and C-8 13C chemical shifts (H. O. Kalinowski, 1988, supra).

Examination of the chemical shift and ROESY data indicated that there was no significant difference in the overall structures of these samples. Nitrogen protonation appears to occur with the N—H proton occupying an axial geometry. However, nitrogen protonation does appear to have made the ring conformations more rigid and adopt the structure shown below:

This conclusion arose from the observation of a 0.7 Hz five-bond coupling between H-1 and H-5e. Spin decoupling experiments confirmed this coupling interaction. Long-range couplings of this type are highly stereospecific and require all the atoms in the coupling pathway to be in a co-planar zig-zag or "W"—type structure. The conformation of five-membered rings is generally more flexible even in large structures such as steroids. Protonation must therefore fix the geometry of the atoms in the long-range coupling pathway as shown in order to produce the observed splitting on the H-1 and H-5e multiplets. The more rigid structure may also account for the changes in the vicinal coupling constants in the five-membered ring in the SWHCl sample (Table 8).

In conclusion, the $^1$H and $^{13}$C chemical shifts of swainsonine hydrochloride and its nitrogen protonated analog have been completely assigned and most of the $^1$H—$^1$H coupling constants have been reported for the well-resolved multiplets. The most significant structural difference between the two samples was the more rigid conformation of the SWHCl molecule as indicated by the long-range $^1$H spin coupling interactions.

Example 8

Preformulation Studies

Preformulation studies of swainsonine hydrochloride, bulk drug substance, and in combination with powder and semisolid fill gelatin capsules were conducted with respect to the following: hygroscopicity, pH, stability, and solubility. The compound was found to be highly hygroscopic. The studies performed on the bulk drug showed that the compound absorbed approximately 8% (w/w) and 24% (w/w) of water in the first 2 and 8 hours, respectively at 75% RH and converted into a semi-solid. At 20% and 50% RH it absorbed 1.9% and 2.1% of water by Karl Fischer after 48 hours of storage. The moisture uptake diminishes when anhydrous powder excipients (e.g. lactose anhydrous and mannitol powder) are used to formulate the pharmaceutical active into a hard capsule.

The compound was highly soluble in aqueous and hydrophilic vehicles. Therefore for soft gelatin capsule formulations hydrophilic vehicles are preferred. The use of a co-solvent such as glycerin or propylene glycol in PEGs may be feasible for liquid or semisolid fills.

The results of a pH study demonstrated that the compound is stable in buffered solutions at pH 4 and 7 under ambient and stressed (40° C. and 50° C.) storage conditions.

Example 9

NMR of Swainsonine Hydrochloride Bulk Drug Substance

Proton nuclear magnetic resonance (NMR) and homonuclear corrrelation spectroscopy (COSY) spectra were obtained for (-)-(1S,2S,8R,8aR)-1,2,8-trihydroxyoctahydro-indolizidine hydrochloride salt (swainsonine hydrochloride, white to off-white crystalline solid, molecular weight 209.66, pKa 7.4, melting range 189–190° C.) in deuterated water ($D_2O$). $D_2O$ was also used as the internal reference at 4.60 ppm. The peak assignments are based upon the proton NMR spectra and the COSY spectral couplings, as determined in Example 7. Differentiation of axial and equatorial protons was achieved by examination of the vicinal coupling constants and the general observation that in six-membered rings axial protons are usually shielded relative to the equatorial protons. The methylene protons at C-3 were assigned to pseudo-axial and pseudo-equatorial positions by 2-D ROSEY experiments.

The carbon NMR spectra, attached proton test (APT) and heteronuclear spin quantum coherence (HSQC) spectra were obtained for (-)-(1S,2S,8R,8aR)-1,2,8-trihydroxyoctahydro-indolizidine hydrochloride salt (swainsonine hydrochloride, white to off-white crystalline solid, molecular weight 209.66, pKa 7.4, melting range 189–190° C.) in $D_2O$. The peak assignments based upon the carbon NMR spectra, the DEPT, and the HSQC spectral interpretation are shown in Table 10. The assignments were based on spectral information found in Nakanishi, K., One-dimensional NMR Spectra by Modem Pulse Techniques, University Science Books, Tokyo, Japan, 1990.

Example 10

Quantitative Microanalysis

Elemental microanalysis (CHN) was performed on (-)-(1S,2S,8R,8aR)-1,2,8-trihydroxyoctahydro-indolizidine hydrochloride salt (swainsonine hydrochloride, white to off-white crystalline solid, molecular weight 209.66, pKa 7A, melting range 189–190° C.) using a Perkin Elmer 2400 combustion analyzer. Chlorine analysis was performed by potentiometric titration. The results are shown in Table 11.

Example 11

Infrared Absorption Spectrum

The Fourier Transform Infrared (FTIR) spectrum of (-)-(1S,2S,8R,8aR)-1,2,8-trihydroxyoctahydro-indolizidine hydrochloride salt (swainsonine hydrochloride, white to off-white crystalline solid, molecular weight 209.66, pKa 7.4, melting range 189–190° C.) taken in a pellet was obtained. The major absorption bands were consistent with the structure for the compound, and assignments of the characteristic absorption bands are listed in Table 12. These assignments were based on spectral information found in Silverstein, R. M., Bassler, G. C., and Morrill, T. C. Spectrometric Identification of Organic Compounds, $3^{rd}$. ed., John Wiley & Sons, New York, 1974, Chapter 3 and in Introduction to Spectroscopy, by Pavia, D. L. Lampman, G. M. and Kriz, G. S., Saunders Golden Sunburst Series Chapter 2.

Example 12

Ultraviolet Absorption Spectra

The ultraviolet absorption spectra of (-)-(1S,2S,8R,8aR)-1,2,8-trihydroxyoctahydro-indolizidine hydrochloride salt (swainsonine hydrochloride, white to off-white crystalline solid, molecular weight 209.66, pKa 7.4, melting range 189–190° C.) exhibited no absorption peaks in the UV region examined from 200 nm to 300 mn in the HPLC peak purity evaluation.

Example 13

Figure 5:
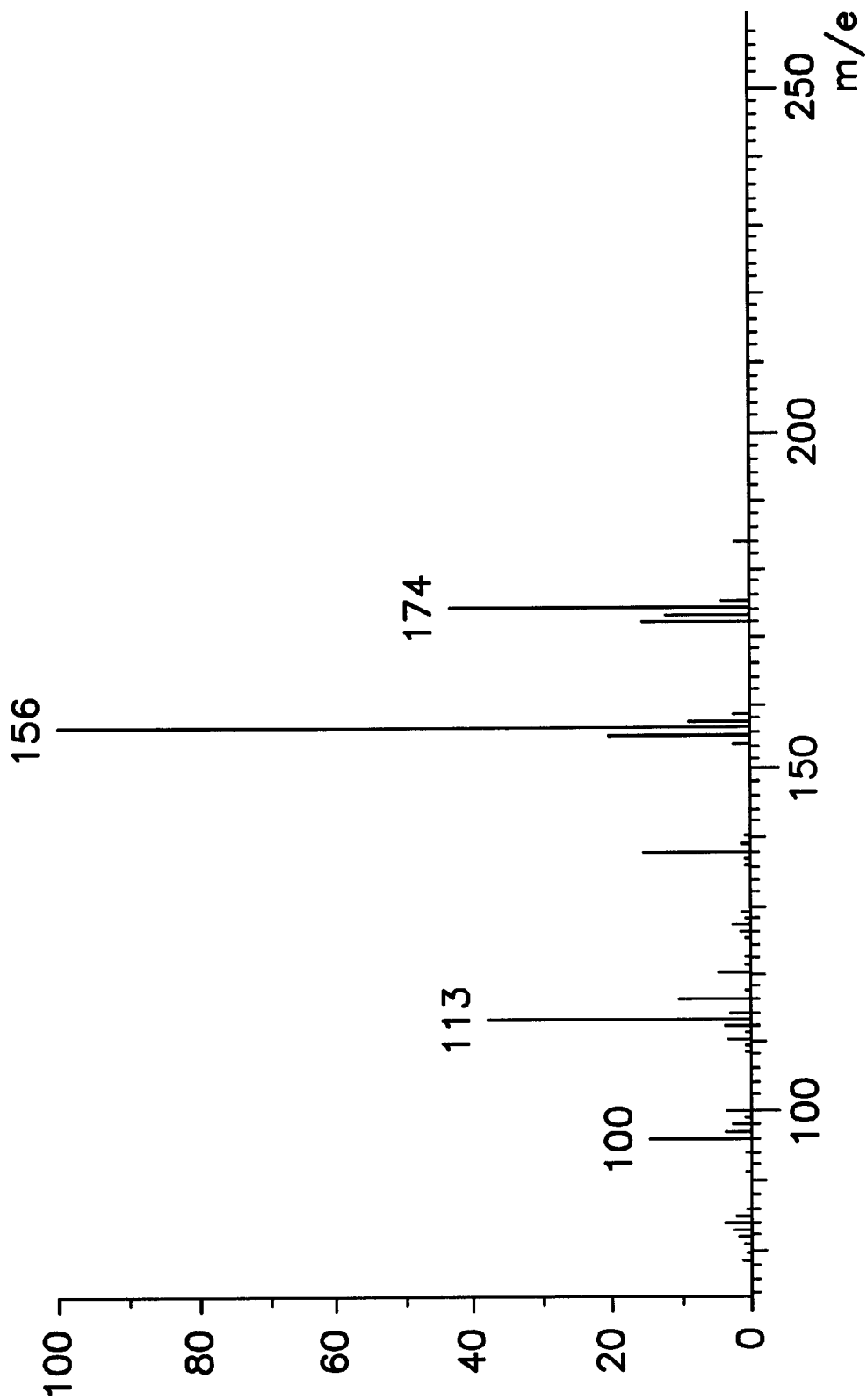

Mass Spectrometry (-)-(1S,2S,8R,8aR)-1,2,8-trihydroxyoctahydro-indolizidine hydrochloride salt (swainsonine hydrochloride, white to off-white crystalline solid, molecular weight 209.66, pKa 7.4, melting range 189–190° C.) was characterized by chemical ionization (Cl)(methane) mass spectrometry on a high resolution VG ZAB IS double focusing magnetic sector instrument. The spectrum is shown in FIG. 5 and the fragmentation scheme is shown in Table 13.

Example 14

X-Ray Powder Diffraction of Swainsonine Hydrochloride Dried for Formulations

A dried sample of swainsonine hydrochloride was shown to be crystallographically similar to the original bulk drug substance. The X-ray powder diffraction studies showed that the use of a zero background sample mounting technique yields a reproducible, characteristic powder pattern for the drug.

Example 15

Thermal Analysis

The differential scanning calorimetry (DSC) thermogram for (-)-(1S,2S,8R,8aR)-1,2,8-trihydroxyoctahydro-indolizidine hydrochloride salt (swainsonine hydrochloride, white to off-white crystalline solid, molecular weight 209.66, pKa 7.4, melting range 189–190° C.) exhibited an enotherm of melt from about 187.5–190.5° C. when heated at 5° C./min. under a nitrogen purge of 45 mL/min. Thermogravimetric analysis (TGA) showed a weight loss of about 0.20% to 160° C. and an endotherm of melt from 187.6–190.5° C. when heated at 5° C./min. under a nitrogen purge of 40 mL/min.

Example 16

High Performance Liquid Chromatography (HPLC)

Figure 6:
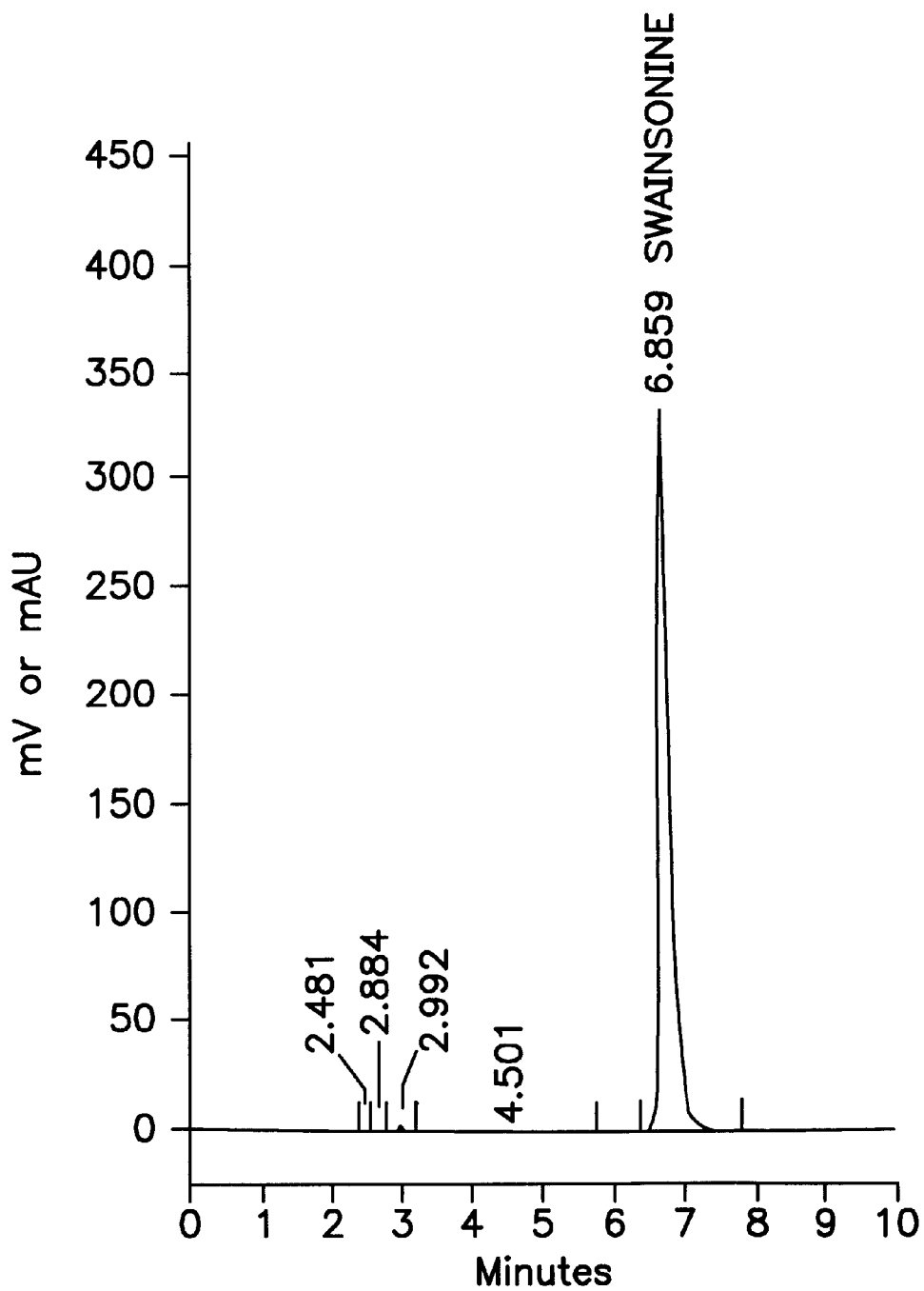

A reversed-phase isocratic high performance liquid chromatographic (HPLC) procedure was developed to assay both the potency and related substances of the drug substance. Quantitiation of drug substance was accomplished by comparison to an external standard of the substance. The related substances were quantified by area percent. The chromatographic procedure for potency and related substances separated the drug substance from its synthetic precursors and potential impurities. The pertinent chromatographic conditions for the HPLC are as follows: Column: Prodigy 5μ ODS-2 (25 cm×4.6 mm ID); Mobile Phase: Acetonitrile:Buffer (10 mM $KH_2PO_4$, pH=9.0) 5:95; Flow Rate: 1.0 mL/minute; Injection Volume: 10 μL; Detection: UV, 205 nm; Temperature: Ambient; Sample Concentration: 1.0 mg/ml; Sample Diluent: Mobile Phase. A representative chromatogram is shown in FIG. 6.

Example 17

Method for Determining Inhibition of Golgi and Lysosomal Mannosidase II In Vitro The test compound swainsonine is prepared by 0.4 serial dilution of a 40 μM stock. Present in each determination is 10 μl diluted test compound, 25 μl of 10 mM paranitrophenyl mannopyranoside, 200 mM sodium acetate, pH 5.6 and 15 μl of purified rat liver Golgi mannosidase II. After incubating the reaction for 60 minutes at 37° C., the reaction is quenched with 50 μl of 0.5 M sodium carbonate. Absorption is read at 405 mn. After subtracting the blank from positive controls and samples, the samples are normalized against the positive control mean using a variable slope, sigmoidal curve fit, with bottom=0, top=100. The signal is proportional to the amount of products from the uninhibited reaction. The calculated $IC_{50}$ for inhibition of purified Golgi mannosidase II by swainsonine hydrochloride is 0.068±0.021 μM.

The effects of the compounds of the invention on lysosomal mannosidase were measured by adding (10 μl) of the compounds into 96 well Elisa plates followed by the addition of 200 mM sodium acetate pH 5.0 and 25 μl of 10 mM p-nitrophenyl α-D-mannospyranoside. 15 μl of lysosomal mannosidase ( about 8 mM/mL) was added to each well and the plates were incubated for 60 min at 37° C. The reaction was stopped by the addition of 50 μl of 0.5M sodium carbonate and formation of p-nitrophenol was measured with a plate set at 405. The calculated $IC_{50}$ for inhibition of lysosomal mannosidase by swainsonine hydrochloride is 0.045±0.010 μM.

Example 18

A. L-PHA Cell Assay for Measuring Inhibition of Mannosidase II in Cells

The test compound swainsonine hydrochloride is prepared by 0.5 serial dilution of a 40 μM stock in 50 μl of 5% fetal bovine serum (FBS) in minimum essential medium (MEM). To 50 μl of diluted test samples in 96 well plates, 10,000 MDAY-D2 tumor cells in 50 μl of 5% FBS in MEM is added to each well. The samples are incubated at 37° C. overnight in a 5% $CO_2$ incubator. Test wells are prepared in duplicate for the addition of 25 μl/well of either 5% FBS in MEM or 5% FBS in MEM containing 100 μg/ml of L-PHA. Samples are again incubated at 37° C. overnight in a 5% $CO_2$ incubator. The viability and/or proliferation of the cells in each well is measured using phenazine methylsulfate (PMS) and (3(4,5-dimethylthiazol-2-yl-5-(3-carboxymethoxyphenyl)-2,4,sulfophenyl)-2H tetrazolium salt ("MTS") as described in the instructions of the Promega CellTiter 96 AQ kit. The absorption is read at 490 nm. The loss of L-PHA toxicity is directly related to entry of the drug into the cells and to inhibition of Golgi mannosidase II, and loss of L-PHA binding carbohydrate structures on the cells surface.

B. High Throughput L-PHA Assay

Materials and Methods

Chemicals. L-PHA, Triton X-100 and para-nitrophenylphosphate were obtained from Sigma; diethanolamine was purchased from Fisher.

Cells. The origin and properties of the DBA-2 strain lymphoreticular tumor MDAY-D2 have been previously described (Kerbel, R S, Florian, M, Man, M S, Dennis, J and McKenzie I F (1980) *J. Natl. Cancer Inst.*, 64, 1221–1230). Cells were cultured in α-modified Eagle's medium containing 2% heat-inactivated fetal calf serum (Gibco BRL) at 37° C. in a 95%$O_2$/5%$CO_2$ humidified atmosphere.

Alkaline Phosphatase Assay. Determinations were carried out using 96-well plates. Each well contained a variable number of MDAY-D2 cells maintained in 125 μl of culture medium supplemented with 2% fetal calf serum. The alkaline phosphatase reaction was initiated by adding 75 μl of assay mixture (1 M diethanolamine buffer, pH 9.8, 2 mM $MgCl_2$, 1% Triton X-100 and 2.5 mM para-nitrophenylphosphate) and incubated at 37° C. for up to 90 min. The reaction was stopped with 80 μl of 3.5 M NaOH. After 15–30 min of colour development, absorbance of the chromogenic product para-nitrophenol was measured at 405 nM using a multiwell scanning photometer (Thermomax Multiplate Reader, Molecular Devices). Background values were determined through assays performed on culture medium alone in the absence of cells and routinely subtracted. Linearity between the absorbance at 405 nM and concentration of para-nitrophenol was in the range 0–2.5 ($\epsilon$=17.23 $mM^{-1}cm^{-1}$).

Screening via L-PHA assays. The procedure was completely automated by using a robotic workstation (Biomek 2000, Beckman) capable of processing nine 96-well plates simultaneously. Determinations were performed in flat bottom 96-well plates (88 samples+8 controls per plate). Each well (columns 1–11) received 10 μl of compound (in 2.5% DMSO), while 10 μl of 2.5% DMSO in water was added to column 12. All 96 wells received 5×10³ MDAY-D2 cells in 90 μl culture medium supplemented with 2% FCS. After 16–20 h incubation at 37° C., 25 μl of L-PHA (100 μg/ml in culture medium) was added to the first 11 columns and to 4 wells of the 12th (positive control). The other 4 wells received 25 μl of medium supplemented with 2% FCS (negative control). Assay plates were maintained for 30–36 h at 37° C., and alkaline phosphatase activity was measured according to the protocol described above using an incubation time of 1 h. Cell density was subconfluent throughout the course of the assay. Proliferation indices were expressed as percentage values, calculated with the formula:

Normalized Signal ($A_{405}$ of sample−mean $A_{405}$ positive control)/ (mean $A_{405}$ negative control−mean $A_{405}$ positive control)

The calculated $IC_{50}$ inhibition of Golgi mannosidase II by swainsonine hydrochloride in cells is 0.057±0.01 μM.

Example 19

Effect of Swainsonine Hydrochloride on Proliferation of SP1.A3, A Mammary Tumor Cell, Proliferation In Vitro The cytokines TGFβ1 and TNFα affect cell growth, lymphoid cell activation, tissue differentiation, and cell death by apoptosis. Whether these cytokines induce cell growth, differentiation or death is however highly cell-type specific and tightly regulated during normal differentiation. Mitogenic effects of TGFβ and TNFα have been reported for melanoma, colon carcinoma and ovarian cancer. Growth factor mediated proliferation can be elicited directly through its signaling pathway or by enhancement of other growth factor receptor expression.

SP1.A3a mouse mammary carcinoma cells were grown for 24 hours in culture medium containing 10% bovine serum, with and without swainsonine hydrochloride at a concentration of 0.2 μg/ml. In the following 24 hours cells were maintained in serum-free medium (SFM) with and without swainsonine hydrochloride. Cells were then grown in the absence of growth factors for 6 hours, or exposed to one of the following growth factors: TNFα (tumor necrosis factor-α), TGFβ1 (transforming growth factor-β), TGFα, platelet-derived growth factor (PDGF), epidermal growth factor (EGF). Tritiated thymidine was added for a final 18 hours, cells were harvested using a multiple-cell harvester and radioactivity was measured in a β-counter as a measure of cell proliferation.

Figure 7:
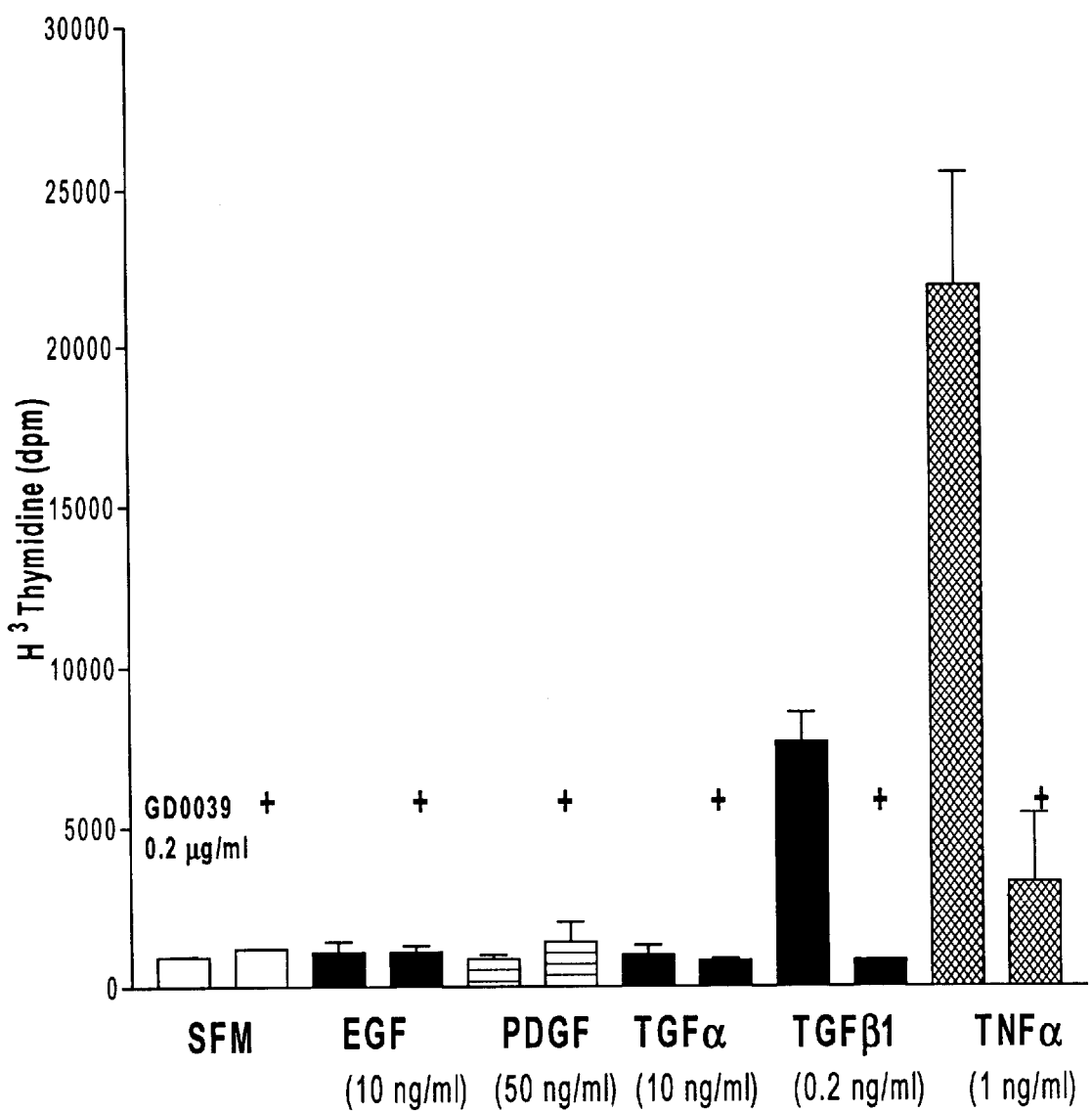

As shown in FIG. 7, proliferation of SP1.A3a cells are stimulated by the growth factors TGF-β1 and TNF-α, and swainsonine hydrochloride treatment suppresses TGF-β1 and TNF-αdependent growth stimulation.

Example 20

Anticancer Activity of Swainsonine Hydrochloride In Vivo

A. Effects of Swainsonine Hydrochloride on the Growth of SP1.A3a Tumor Cells in Mice A metastatic subclone of the SP1 tumor line (A3a), mouse mammary adenocarcinoma was maintained in exponential growth in RPMI 1640 containing 10% FBS. The cells were harvested and resuspended at $1 \times 10^6$/ml or $1 \times 10^7$/ml in PBS and 0.1 ml containing $1 \times 10^5$ injected S.C. into the right flank of 7 week old female CBA/J mice (Jackson Laboratories). Alzet mini-osmotic pumps were implanted subcutaneously, on the opposite side of anesthetized animals. The pumps were primed to deliver saline (control) or 0.5 mg/kg/day of swainsonine hydrochloride over 28 days. Mice were monitored for the appearance of a palpable tumour and subsequent tumor growth was measured using bernier callipers. Tumor weights and the number of lung metastasis were measured on day 42.

Figure 8:
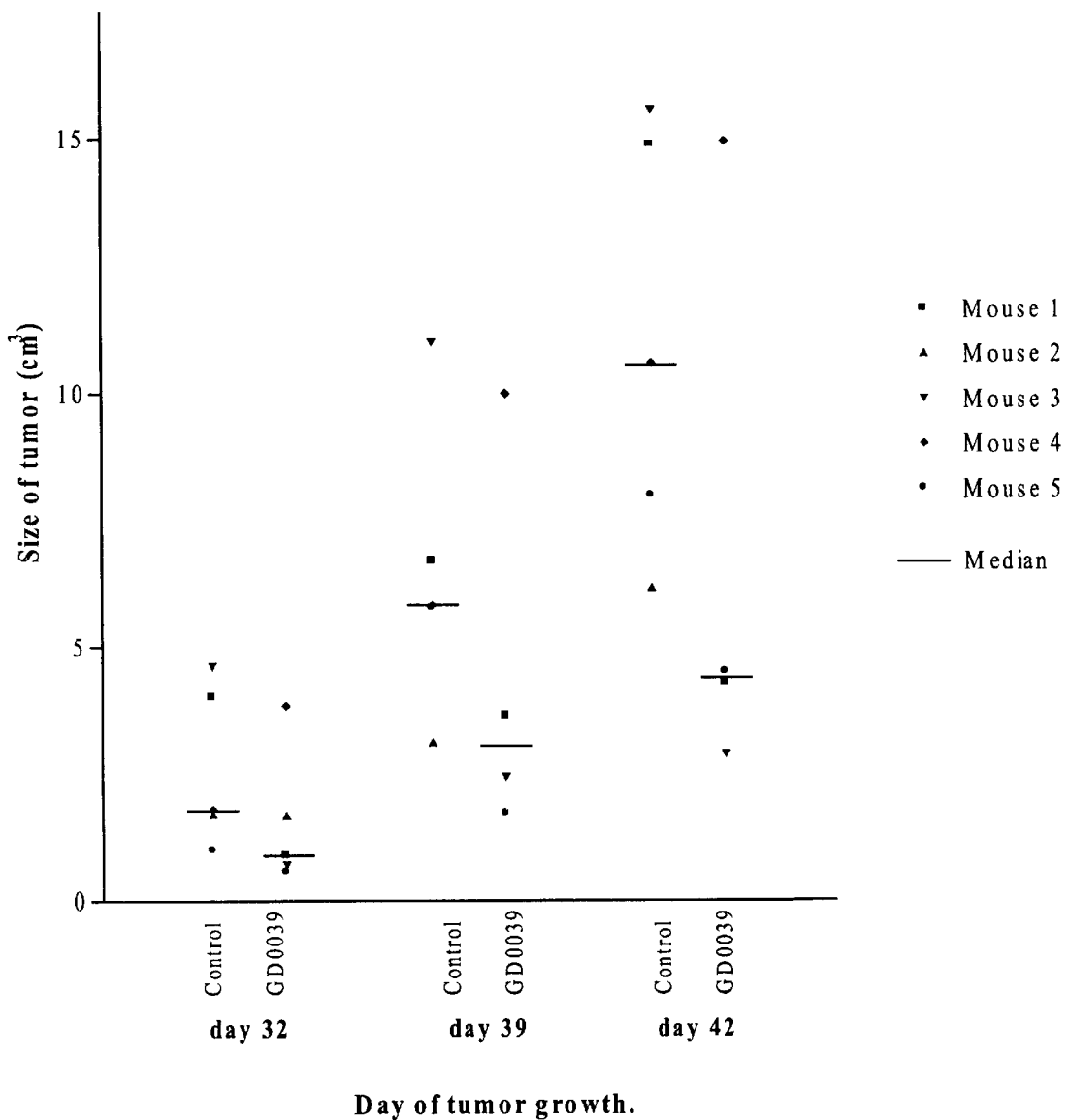

Mean tumour volume on days 32, 39, and 42 of treatment were larger in contol animals (−) then in mice receiving swainsonine hydrochloride via osmotic pumps for 28 days (+) (FIG. 8). The difference in mean tumour volume between the control and the swainsonine hydrochloride treatment groups on days 32, 29, and 42 of treatment were 35%, 27%, and 32%, respectively.

The mean tumour weight determined at the 42 day sacrifice point for the 5 animals in the control group was higher than for the 4 animals in the swainsonine hydrochloride group and were 7.35 g vs. 4.87 respectively. The treated group had one very large tumour.

At the day 42 sacrifice point, the incidence of lung metastasis in control mice was an average of 1.8 nodules/mouse and an average of 0.25 nodules/mouse in swainsonine hydrochloride treated mice.

This experiment confirms the anti-tumor activity of the hydrochloride salt of swainsonine. In fact, the dose used was 8 times lower than that used in the initial experiment performed with swainsonine free base.

B. Effects of Oral Swainsonine Hydrochloride in Drinking Water on the Growth of SP1.A3a Tumor Cells in Mice The experiment was repeated using swainsonine hydrochloride administered in drinking water. SP1.A3a mouse mammary adenocarcinoma were maintained in exponential growth in RPMI 1640 medium containing 10% FBS. The cells were harvested and re-suspended at $3 \times 10^5$/ml in PBS and 0.1 ml containing $3 \times 10^4$ cells injected S.C. into the right flank of 7 week old female CBA/J mice (Jackson Laboratories) (n=25). The mice were subsequently supplied with drinking water alone (n=13) or drinking water containing 10 μg/ml swainsonine hydrochloride (n=12) (equivalent to a dose of 2 mg/kg/day).

Once a palpable tumor was evident, tumor size was measured twice a week using vernier callipers. At the end of the treatment period the tumors were excised and weighed.

Figure 9:
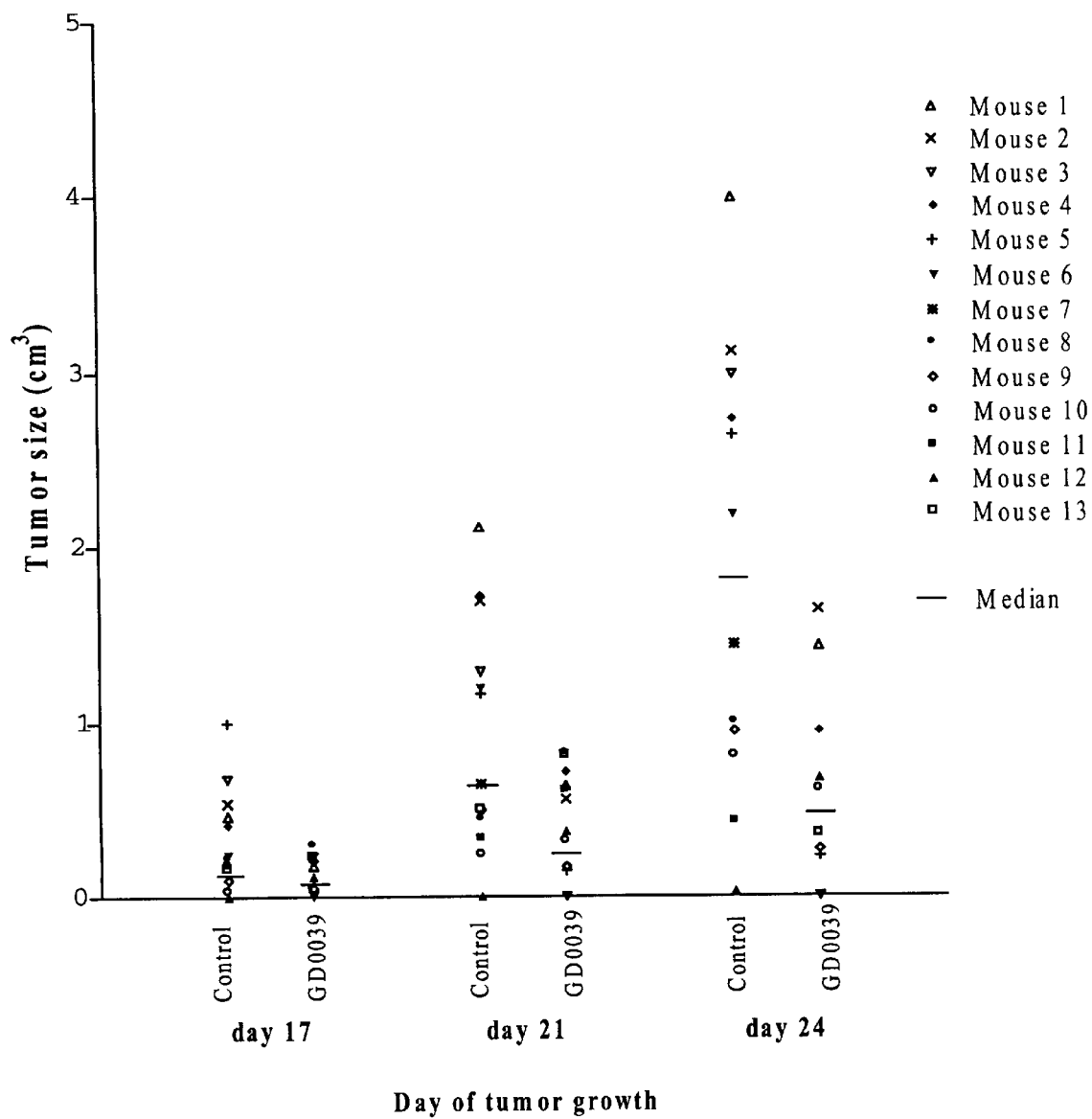

Tumor bearing mice with 10 μg/ml of swainsonine hydrochloride in the drinking water had slower growing tumors than control mice treated with water alone. The results are shown in FIG. 9. The medium tumour size is much smaller for the swainsonine hydrochloride treated mice (+) than the saline treated mice (−). These differences are statistically significant for the time points shown.

The mean tumor weights at 31 days in the treated groups was 1.79 g and in the untreated was 3.33 g.

In conclusion, the experiments demonstrate that swainsonine hydrochloride has both in vitro and in vivo anticancer activity. In addition, the anticancer activity was demonstrated using a much lower dose than previously reported for swainsonine free base.

Example 21

The In Vitro Effect of Swainsonine Hydrochloride and Swainsonine on Murine Bone Marrow Progenitor Cells (CFU-E and CFU-GM)

Materials and Methods

Animals

Pathogen-free C57BL/6 female mice, 8–9 weeks old, obtained from Jackson Laboratories were used. The room environment and photoperiod were controlled: 24° C.; humidity, 50±20%; 12 hr light and 12 hr dark. Mice were housed one per cage with ad libitum accesses to standard pelleted commercial laboratory diet and to sterile (autoclaved) tap water.

Materials

Swainsonine hydrochloride was manufactured by Seres Laboratories, Calif. FBS and methylcellulose (MethoCult M3330) were purchased from Stem Cell Technologies, Inc. (Vancouver. BC). Iscove's modified Dulbecco's medium was prepared using powdered media from Gibco BRL, deionized water and filter sterilization. For the handling of cells, the media was supplemented with 2% FBS and 50 μM β-mercaptoethanol (referred to as IMDM/FBS).

Cell Harvesting

The healthy and GD0039 treated mice were euthanized by $CO_2$ asphyxiation. Bone marrow (BM) cell suspensions were prepared under sterile conditions by flushing both femurs and tibiae with IMDM/FBS using a 26 gauge needle. Single cell suspensions were made up to 10.0 ml IMDM/FBS. The concentration of nucleated cells in each suspension was determined by triplicate counts on a hemocytometer. A portion of the cells was further diluted in media to the appropriate concentration before plating for the progenitor assay.

Progenitor Cell Assay

Colony-forming units (CFUs) were estimated by the methylcellulose method. One milliliter suspensions, containing 2×10⁵ nucleated BM cells, in 0.1 ml of IMDM and 0.9 ml MethoCult (M3330), were plated in triplicate in 35 mm tissue culture dishes. Swainsonine hydrochloride or swainsonine were added to certain plates, in 0.1 ml of IMDM at concentrations of 30 μg/ml and 3 μg/ml, which gave final concentrations of 3 μg/ml. The MethoCult M3330 contains 30% FBS and 10 μg/ml erythropoietin and is designed for the growth of early erythroid progenitor cells (CFU-E), which were scored after 3 days of incubation at 37° C. in a humidified atmosphere containing 5% $CO_2$. For granulocyte-macrophage progenitor cells (CFU-GM), the MethoCult M3230 contains 30% FBS, does not contain any additional growth factors and supports the growth of CFU-GM which are scored after 7 days of incubation at 37° C. in a humidified atmosphere containing 5% $CO_2$. To some plates SCF and/or GM-CSF are added in 0.1 ml of IMDM to give a final concentration of 50 μg/ml or 5 μg/ml (ED50) for SCF and 0.25 μg/ml or 1.7 μg/ml for GM-CSF. Colonies containing more than 20 cells were scored using an inverted microscope with brightfield optics and 40× or 100× magnification.

Results

BM cells of a healthy mouse and mouse dosed with 20 μg/day of swainsonine hydrochloride for four days were analyzed in a CFU assay using M3330 methylcellulose. Both swainsonine hydrochloride and swainsonine significantly increased the number of early CFU-E, counted on day 3, when added to methylcellulose in vitro (Table 14). The high (3 μg/ml) and low (0.3 μg/ml) concentrations of swainsonine hydrochloride and swainsonine stimulated the number of CFU-E to the same extent when added to the BM cells of the control (untreated) mouse. This was a dose dependent effect when using BM from the in vivo swainsonine hydrochloride treated mice.

Both swainsonine hydrochloride and swainsonine stimulate in vitro erythroid progenitor cells approximately at the same rate. At concentrations from 0.03 μg/ml to 10 μg/ml they cause ~3-fold increase in the number of early CFU-E.

Figure 11:
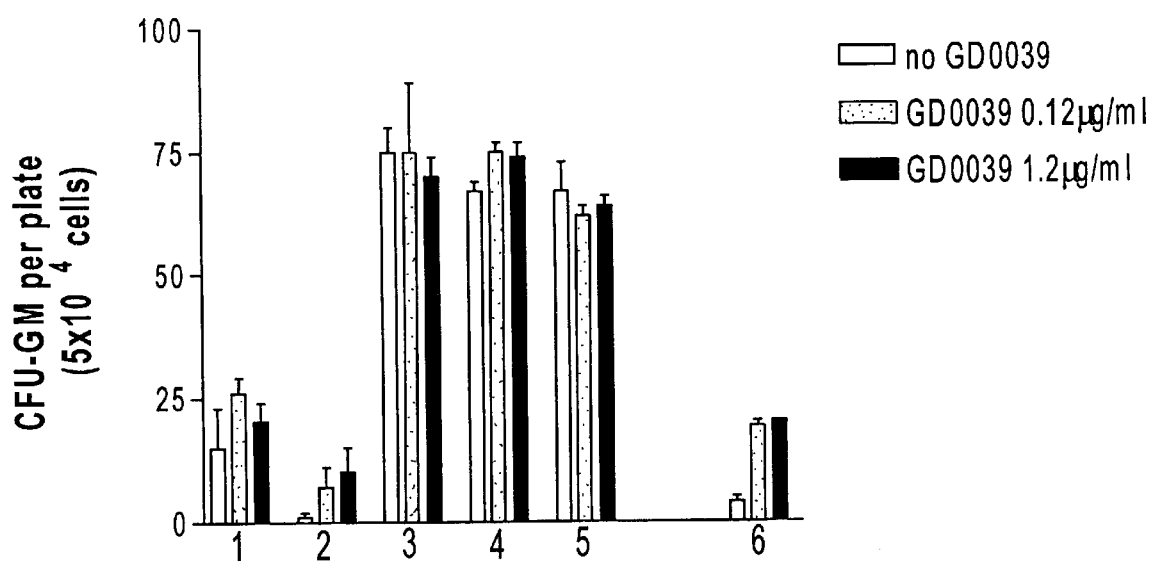

Both swainsonine hydrochloride and swainsonine also stimulate in vitro granulocyte-macrophage progenitor cells (FIG. 11: BM cells from a healthy C57BL/6 mouse were plated in 1.0 ml suspensions obtained from a mixture of 0.8 ml methylcellulose M3230, 0.1 ml cell suspension, 0.1 ml SWHCl and 0.1 ml cytokines: 1—SCF 50 ng/ml, 2—SCF 5 ng/ml, 3—GM-CSF 1.7 μg/ml, 4—GM-CSF 0.25 μg/ml, 5—SCF 50 ng/ml+GM-CSF 0.25 μg/ml, 6—without cytokines). In the absence of specific stimulating factors, swainsonine hydrochloride showed an ~4 fold increase in CFU-GM.

Example 22

Toxicology and Pharmacokinetic Studies

Pharmacological and toxicological studies were conducted with swainsonine hydrochloride. In particular, the following were investigated: (a) pharmacokinetics of the compound in rats and monkeys; (b) acute toxicity at significant multiples of the intended human dose; (c) the toxicity profile of the compound was compared to the literature profile for swainsonine free base; (d) potential for genotoxicity; (e) time course, dose-dependence, tissue sensitivity and reversibility of oligosaccharide accumulation in tissue; and (f) serum AST and relationship to liver histology. The studies indicated that acute toxicity to swainsonine occurs only at very high doses, 13,000 times the intended human dose. Chronic studies indicate that the thyroid and also possibly the kidney could be the sites of reversible accumulation of oligomannosides in lysosomes at the doses proposed for humans.

Example 23

Representative In Vivo and In Vitro Protocols

A. Administration of Swainsonine Hydrochloride for the Inhibition of Lung Metastasis B16F10 melanoma tumor cells are cultured for 48 hours in the presence or absence of swainsonine hydrochloride (0.36 μg/ml) before injection of 10 cells into the lateral tail veins of C57BL mice. Lung nodules are counted on day 24 after injection of tumor cells as described in Dennis, J W, Cancer Res. 46:5131–5136, 1986.

B. Swainsonine Hydrochloride for the Inhibition of Tumor Cell Colonization of the Lung Mice are given drinking water with or without 5.0 μg/ml swainsonine hydrochloride 2 days before tumor cells are injected into the lateral tail vein and maintained on swainsonine hydrochloride for periods of 1–17 days. Lung nodules are counted on day 24 after injection of tumor cells.

C. Inhibition of Human Tumor Growth in Mice

Athymic nude mice injected subcutaneously with MeWo, a human melanoma tumor cell line, are treated with once daily ip injections of sterile saline or 20 μg/mouse of swainsonine hydrochloride in sterile saline. Tumor size is measured twice weekly with callipers and tumor weights are measured 4 weeks after tumor cell injection as per the method of Dennis, J W (Cancer Res. 50:1867–1872, 1990).

D. Determining Synergy of Swainsonine Hydrochloride with the Interferon-inducing Agent Poly (I.C.) for Inhibition of Solid Tumor Growth Mice are provided with drinking water either with or without swainsonine hydrochloride (3.0 μg/ml) 2 days before 10⁵ MDAY-D2 tumor cells are injected. Tumor diameters are measured with callipers twice weekly, then on day 15 after tumor cell injection, tumors are excised and weighed. The tumor growth rate and tumor weight on day 15 in mice given swainsonine hydrochloride supplemented drinking water and/or two i.p. injections of poly (I.C.) are compared as described in Dennis J W Cancer Res. 46:5131–5136, 1986.

E. Enhancement of the Anti-proliferative Effect of Interferon In Vitro By Swainsonine Hydrochloride HT29m, SN 12C11 human carcinoma cells or MeWo melanoma cells are seeded into 5% FBS in MEM tissue culture medium at 10³/ml in the presence and absence of swainsonine hydrochloride approximately (1.2 μg/ml) either with or without 1000 IU/ml of human interferon alpha-2 (intronA, Schering-Plough). The cells are cultured at 37° C. in a 5% $CO_2$ atmosphere and on day 5 the cell number is determined. The method is as described by Dennis, J. W. JNCI 81:1028–1033, 1989.

F. In Vitro Progenitor Cell Assay

At specified times after treatment with between 0.7 and 5.0 μg/ml of swainsonine hydrochloride, control, and treated mice are killed by cervical dislocation. Bone marrow (BM) and spleen cells from each are processed according to the procedures of the GIBCO-BRL Mouse Bone Marrow Stem Cell Proliferation Kit (Cat. #3827SA, Grand Island, N.Y.). The potential colonies that form in the semi-solid medium are the CFU-GEMM, the CFU-GM, and the BFUs. The plates are incubated for 10–14 days at 37° C. in a humidified atmosphere of 5% $CO_2$ and 95% air, and colonies consisting of at least 40 cells are enumerated using an inverted microscope (20× magnification) to demonstrate stimulation of hematopoietic progenitor cell growth.

G. Bone Marrow Proliferation Assay

Mice are treated with either 3 μg/ml of swainsonine hydrochloride in their drinking water or injected with 20 μg/mouse of swainsonine hydrochloride daily for 2–6 days. Proliferation is assessed by the incorporation of [$^3$H]-thymidine (5 μCi/ml) for 18 hours at 37° C. into cultures containing equal numbers of freshly isolated BM cells in complete medium. The radiolabeled cells are collected with the aid of a cell harvester onto glass filters, and radioactivity is determined using a liquid scintillation counter. Cellularity of the bone marrow is also determined by using the Coulter counter to directly count BM cells after they are flushed from the tibias and femurs.

H. In Vivo Progenitor Assay: Spleen Colony Formation Assay

Mice (10–14 weeks old) are x-irrradiated for a total whole body exposure of 700cGY. The irradiated mice are maintained on sterile drinking water approximately 3 μg/ml) and are given antibiotics to minimize mortality from infection. The number of BM stem cells is estimated by the method of Till and McCulloch, which is based on the ability of intravenously injected progenitor stem cells to form colonies in the spleens of recipient mice previously exposed to a lethal dose of whole-body irradiation. The number of CFUs is proportional to the number of pluripotent hematopoietic stem cells present in the hematopoietic graft. Ten days after transplantation, recipient mice are sacrificed, their spleens are removed and fixed in Bouin's solution, and grossly visible colonies are counted.

I. Bone Marrow Transplant and Repopulation

Prior to transplantation with bone marrow cells, mice are pre-treated with either a lethal dose of a chemotherapeutic agent or a lethal dose of x-irradiation, as described in White et al (Cancer Communications 3:83, 1991) and Oredipe et al. (JNCI 83:1149, 1991). Mice aged 10–14 weeks, are irradiated using Phillips RT 250 x-ray machines (two opposing therapeutic 250 Kvp x-ray machines, 235 KV, 15 mA, filtration 0.25 copper and 0.55 aluminum, with a half layer of 0.99 mm copper). Irradiation occurs with a dose rate of 126 cGy/min (63 cGy/min×2) for 5 minutes and 33 seconds, for a total whole body exposure of 700 cGy. This level of irradiation exposure is within the range described as being lethal for mice. After x-irradiation, animals are infused with $10^5$ bone marrow cells freshly prepared from either control or swainsonine hydrochloride-treated donor mice. The swainsonine hydrochloride-treated donor mice receive approximately 20 μg/ml of swainsonine hydrochloride for 6 days. Recipient mice are monitored for survival over a period of 30 to 50 days.

J. Th1 Immune Response: Natural Killer (NK) and Lymphokine-activated Killer (LAK) Cell Assays Human peripheral blood mononuclear cells (PBMCs) are isolated from whole blood using standard methods (Rees et al; J. Immunol Meths., 62:79–85, 1983; or Sedman et al, Br. J. Surg. 75: 976–981, 1988). The PBMCs are seeded into six-well plates in 5 ml cultures at a concentration of 1.5 million cells per ml either alone (control) or with varying concentrations of swainsonine hydrochloride, together with 1000 International Units (IU)/ml of IL-2 for three days for the LAK assay or 1000 IU/ml interferon-alpha overnight for the NK assay. The NK cell activity of the cultured PBMCs is measured in a $Cr^{51}$ release assay using the K562 cell line (NK cell-sensitive) as target cells. LAK cell activity is measured using $Cr^{51}$-labeled Daudi cell line (NK cell-resistant) as targets.

K. Measurement of STAT Levels and Activation as a Means of Differentiating Th1/Th2 Immune Responses To measure the level and activation of STATs, DBA/2 mice are treated for 6–9 days with 20 μg/mouse/day of swainsonine hydrochloride followed by a single intraperitoneal (i.p) injection of either sterile saline or 100 μg of poly IC (i.e., dsRNA, a surrogate for virus) in sterile saline. Two hours later an optimal time for STAT activation, spleens of the mice are homogenized and cytosolic and nuclear cell extracts are prepared. STAT protein levels are measured in the cytosolic and nuclear fractions by Western blot analysis. STAT phosphorylation (i.e. activation) is measured following immunoprecipitation using anti-phosphotyrosine antibodies. Mice treated with 20 μg/day ip of swainsonine hydrochloride salt had enhanced STAT1 cytosolic protein levels while STAT3 remained unchanged (FIGS. 10A to 10C).

Figure 10A:
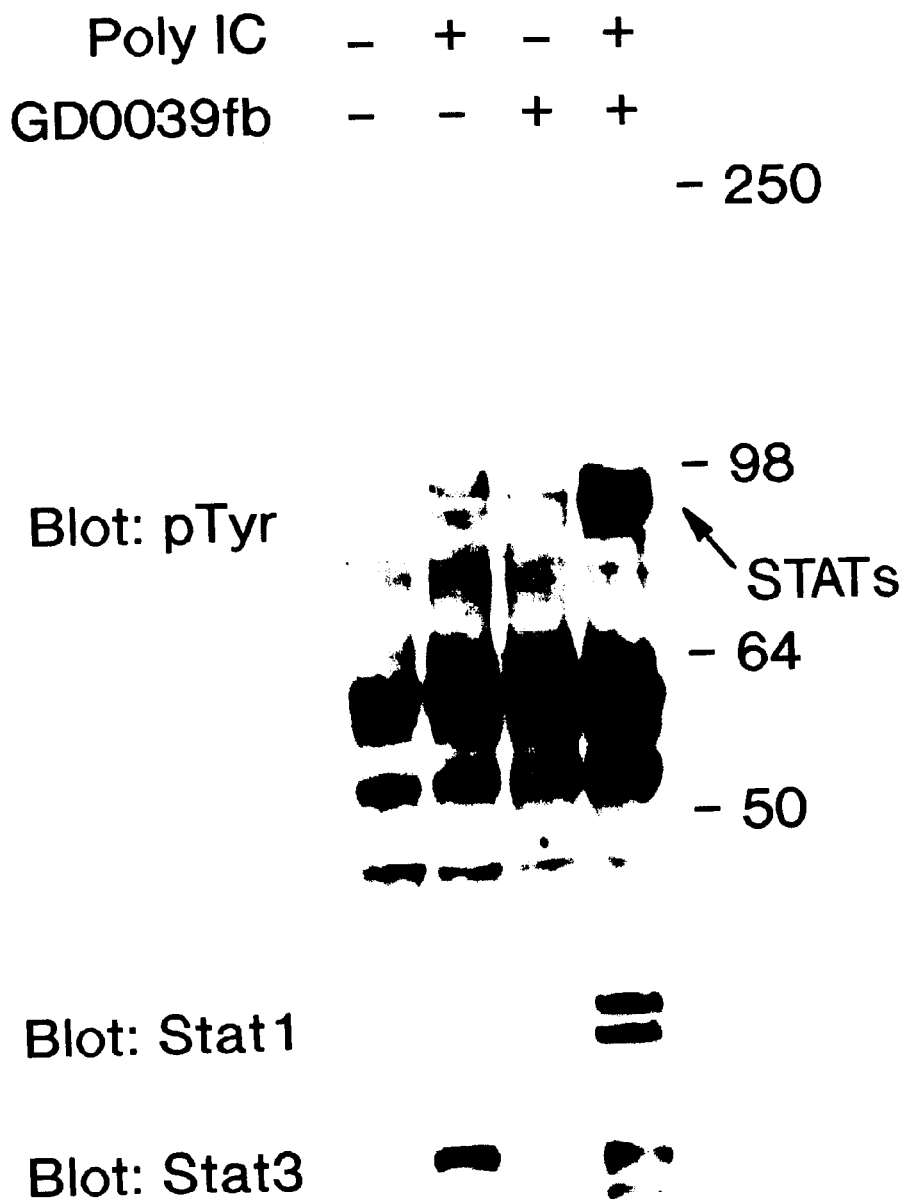
Figure 10B:
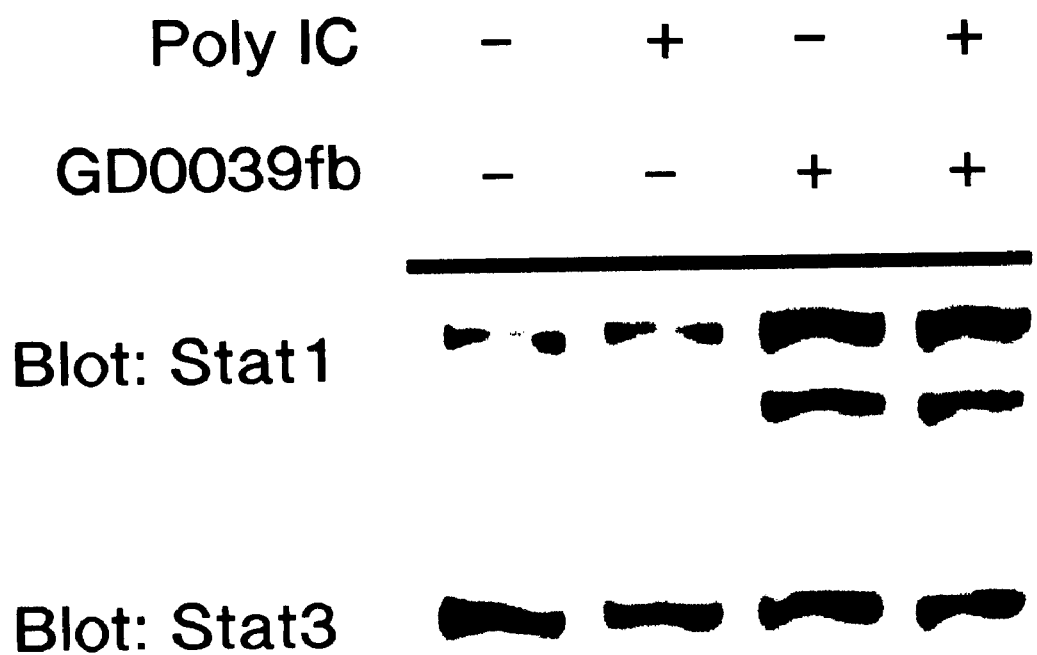
Figure 10C:
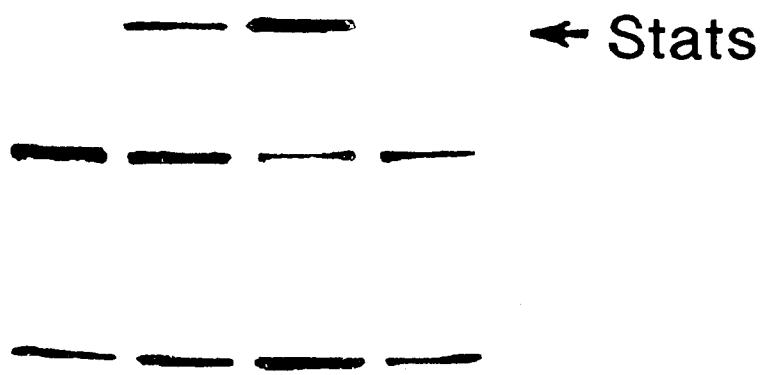

The following is a detailed description of FIGS. 10A to 10C: FIG. 10A illustrates that SW hydrochloride increases the activation of STAT1 in spleen following treatment of DBA/2 mice with Poly IC. DBA/2 mice received daily ip injections of SW hydrochloride (20 μg/day) for 10 days. On day 11 the mice were injected with Poly IC (100 μg/mouse) or an equivalent volume of PBS 2 h before being sacrificed. Spleen and liver tissues were collected and immediately frozen in liquid nitrogen. Nuclear extracts were prepared and analyzed (8 μg) by immunoblotting with the indicated antibodies. Similar results were observed in liver (data not shown). FIG. 10B. Cytosol extracts were prepared and analyzed (20 μg) by immunoblotting with the indicated antibodies. Spleen nuclear extracts were prepared and analyzed (8 μg) by immunoblotting with anti-phosphotyrosine antibodies. FIG. 10C. STAT activation, and turnover of activated STATs occurs rapidly in response to the type I IFN inducer poly IC. DBA/2 mice received a single ip injection with Poly IC (100 μg/mouse) and were sacrificed at the indicated times.

Alternatively, an ELISA or ELISA-like assay can be employed to detect STAT levels and activation in human peripheral blood. STAT dimers, bound to DNA promoter consensus sequences which have been attached to plastic microtiter plates, are detected using anti-STAT antibodies coupled to alkaline phosphate (or other appropriate tag). Samples of human peripheral blood lymphocytes are lysed, and cell extracts prepared by methods known in the art. Bound, activated STAT protein levels are quantitated optically after reaction of bound STAT protein with an appropriate detector (e.g. if alkaline phosphatase coupled antibodies are used then a colorimetric substrate reactive with alkaline phosphate may be used for detection).

L. Activity in Mouse Model of Hepatitis

Drug activity against viral hepatitis may be determined by infecting mouse strains with mouse hepatitis virus-3 (MHV-3). Previous studies with MHV-3 have focused on mouse strains which develop fulminant hepatitis (Balb\cJ) or display resistance (A/J) to MHV-3 (Yuwaraj et al., 1996).

The CH3/HeJ strain, which develops chronic hepatitis in response to MHV-3 infection is treated with either saline or swainsonine hydrochloride (20 μg/mouse/day) alone or in combination with IFN. Before and during treatment, the levels and activation status of STATs is measured (as described under "K") as well as serum cytokine levels, viral load and survival.

M. Activity in Patients with Chronic Hepatitis C

The response to treatment with swainsonine hydrochloride or swainsonine hydrochloride plus interferon-alpha in patients with chronic hepatitis C can be monitored by a decrease in viral load and serum liver alanine aminotransferase (ALT) measured during treatment, for example at 3, 6, and 12 months. Improvement in liver histology can also be assessed by performing biopsies before and after treatment.

Swainsonine hydrochloride is administered orally, twice daily, at doses between 50 and 200 µg/kg either alone, or in combination with alpha-interferon, which is administered at doses of 1 to 3 MU three times weekly. During this time, swainsonine hydrochloride may be administered continuously or intermittently (e.g. 2 weeks on, one week off). The response in patients receiving swainsonine hydrochloride is compared to the response in patients receiving placebo or alpha-interferon.

Detection of hepatitis C viral RNA in serum, liver, and peripheral blood mononuclear cells is performed by the reverse transcriptase-polymerase chain reaction method (RT-PCR), using primer specific for the highly conserved, 5'-untranslated region (UTR) for qualitative or, with appropriate internal control RNA, quantitative detection. The second method is a signal amplification or branched chain DNA (bDNA) assay. Viral nucleic acids are hybridized to microtiter plates and reacted with virus-specific extender probes followed by bDNA polymers.

For improvement in liver histology, the Histologic Activity Index based on a scoring system developed by Knodell et al (Hepatology 1981, 1:431–435), assigns grades in four categories: periportal necrosis, interlobular necrosis, portal inflammation and fibrosis. Alternatively, a system based on grading hepatic inflammation (0–4) and staging fibrosis (0–4) can be used (Scheuer P J, J. Hepatol 1991; 13:372–374).

N. Hemorestoration/Chemoprotection

Cellular and animal models of hemorestoration/chemoprotection are described in Oredipe et al, 1991, supra, and White et al, 1991, supra.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Atomic coordinates (×10$^4$) and equivalent isotropic displacement parameters (A$^2$ × 10$^3$) for Swainsonine HCl.
U(eq) is defined as one third of the trace of the orthogonalized Uij tensor.

|  | x | y | z | U(eq) |
|---|---|---|---|---|
| N(1) | .8032(3) | 9646(3) | 6106(2) | 33(1) |
| C(2) | 6986(5) | 9036(4) | 6905(3) | 48(1) |
| C(3) | 5928(4) | 10205(5) | 7343(3) | 55(1) |
| C(4) | 6957(5) | 11498(5) | 7671(3) | 48(1) |
| C(5) | 8049(4) | 12062(3) | 6834(2) | 38(1) |
| O(5) | 9065(4) | 13168(3) | 7207(2) | 51(1) |
| C(6) | 9129(3) | 10845(3) | 6465(2) | 31(1) |
| C(7) | 10278(3) | 11045(3) | 5593(2) | 33(1) |
| O(7) | 9428(3) | 11616(3) | 4776(2) | 42(1) |
| C(8) | 10742(4) | 9476(3) | 5379(2) | 36(1) |
| O(9) | 11297(3) | 9197(3) | 4412(2) | 47(1) |

TABLE 1-continued

| C(9) | 9150(4) | 8634(3) | 5574(3) | 39(1) |
|---|---|---|---|---|
| Cl | 5025(1) | 10142(1) | 4669(1) | 48(1) |

Bond lengths [A] and angles [deg] for Swainsonine.

| N(1)-C(2) | 1.493(4) | N(1)-C(9) | 1.498(4) |
|---|---|---|---|
| N(1)-C(6) | 1.514(4) | C(2)-C(3) | 1.513(6) |
| C(3)-C(4) | 1.538(6) | C(4)-C(5) | 1.537(5) |
| C(5)-O(5) | 1.418(4) | C(5)-C(6) | 1.523(4) |
| C(6)-C(7) | 1.520(4) | C(7)-O(7) | 1.413(4) |
| C(7)-C(8) | 1.548(4) | C(8)-O(8) | 1.416(4) |
| C(8)-C(9) | 1.534(4) | | |
| C(2)-N(1)-C(9) | 116.8(3) | C(2)-N(1)-C(6) | 112.4(2) |
| C(9)-N(1)-C(6) | 105.9(2) | N(1)-C(2)-C(3) | 109.3(3) |
| C(2)-C(3)-C(4) | 112.4(3) | C(5)-C(4)-C(3) | 111.5(3) |
| O(5)-C(5)-C(6) | 109.6(3) | O(5)-C(5)-C(4) | 108.6(3) |
| C(6)-C(5)-C(4) | 108.4(3) | N(1)-C(6)-C(5) | 109.2(2) |
| N(1)-C(6)-C(7) | 101.4(2) | C(5)-C(6)-C(7) | 121.0(3) |
| O(7)-C(7)-C(6) | 111.4(2) | O(7)-C(7)-C(8) | 109.3(2) |
| C(6)-C(7)-C(9) | 100.2(2) | O(8)-C(8)-C(9) | 109.4(3) |
| O(8)-C(8)-C(7) | 115.3(3) | C(9)-C(8)-C(7) | 104.7(2) |
| N(1)-C(9)-C(8) | 105.3(2) | | |

Hydrogen coordinates (×10$^4$) and isotropic displacement parameters (A$^2$ × 10$^3$) for Swainsonine.

|  | x | y | z | U(eq) |
|---|---|---|---|---|
| H(1) | 7389(48) | 10037(38) | 5663(27) | 33(8) |
| H(5) | 7411(49) | 12410(39) | 6262(28) | 47(10) |
| H(6) | 9705(49) | 10490(41) | 7048(28) | 37(9) |
| H(7) | 11252(47) | 11628(39) | 5760(27) | 37(9) |
| H(8) | 11572(42) | 9195(36) | 5839(25) | 28(8) |
| H(21) | 6370(46) | 8215(38) | 6605(27) | 37(9) |
| H(22) | 7652(62) | 8686(47) | 7342(30) | 49(12) |
| H(31) | 5052(63) | 10540(54) | 6823(39) | 68(14) |
| H(32) | 5321(69) | 9843(51) | 7905(37) | 72(15) |
| H(41) | 6173(69) | 12259(51) | 7869(34) | 70(15) |
| H(42) | 7587(69) | 11289(56) | 8201(38) | 71(15) |
| H(91) | 8558(49) | 8330(37) | 4953(28) | 40(10) |
| H(92) | 9352(46) | 7757(36) | 5942(23) | 31(8) |
| H(50) | 9343(70) | 13606(56) | 6751(38) | 65(16) |
| H(70) | 9520(65) | 12384(60) | 4878(40) | 59(14) |
| H(80) | 12087(62) | 9412(51) | 4425(36) | 54(14) |

TABLE 2

Atomic coordinates (×10$^4$) and equivalent isotropic displacement parameters (A$^2$ × 10$^3$) for Swainsonine HBr.
U(eq) is defined as one third of the trace of the orthogonalized Uij tensor.

|  | x | y | z | U(eq) |
|---|---|---|---|---|
| N(1) | 2781(6) | 4325(5) | 3064(3) | 28(1) |
| C(2) | 992(6) | 4319(8) | 3007(4) | 38(2) |
| C(3) | 391(7) | 5620(9) | 3648(4) | 47(2) |
| C(4) | 981(7) | 5479(8) | 4654(4) | 39(2) |
| C(5) | 2802(7) | 5331(8) | 4707(4) | 33(1) |
| O(5) | 3193(5) | 4981(7) | 5655(3) | 53(1) |
| C(6) | 3322(6) | 3995(6) | 4075(4) | 25(1) |
| C(7) | 5074(7) | 3656(6) | 3922(3) | 30(1) |
| O(7) | 5942(4) | 4996(6) | 3674(3) | 34(1) |
| C(8) | 5017(7) | 2545(6) | 3067(4) | 32(1) |
| O(8) | 6469(6) | 2363(5) | 2578(3) | 40(1) |
| C(9) | 3627(9) | 3153(8) | 2464(4) | 41(2) |
| Br | 2065(1) | −250(1) | 4058(1) | 42(1) |

Bond Lengths [A] and angles [deg].

| N(1)-C(9) | 1.498(7) | N(1)-C(2) | 1.506(7) |
|---|---|---|---|
| N(1)-C(6) | 1.525(6) | C(2)-C(3) | 1.528(9) |
| C(3)-C(4) | 1.509(8) | C(4)-C(5) | 1.538(8) |
| C(5)-O(5) | 1.410(6) | C(5)-C(6) | 1.522(8) |
| C(6)-C(7) | 1.517(7) | C(7)-O(7) | 1.411(6) |
| C(7)-C(8) | 1.542(7) | C(8)-O(8) | 1.411(7) |
| C(8)-C(9) | 1.538(8) | | |

TABLE 2-continued

| | | | |
|---|---|---|---|
| C(9)-N(1)-C(2) | 116.2(5) | C(9)-N(1)-C(6) | 105.2(4) |
| C(2)-N(1)-C(6) | 110.3(4) | N(1)-C(2)-C(3) | 107.2(5) |
| C(4)-C(3)-C(2) | 113.0(6) | C(3)-C(4)-C(5) | 112.3(5) |
| O(5)-C(5)-C(6) | 109.1(5) | O(5)-C(5)-C(4) | 107.2(5) |
| C(6)-C(5)-C(4) | 108.6(5) | C(7)-C(6)-C(5) | 120.6(4) |
| C(7)-C(6)-N(1) | 101.1(4) | C(5)-C(6)-N(1) | 108.8(4) |
| O(7)-C(7)-C(6) | 112.3(4) | O(7)-C(7)-C(8) | 109.4(4) |
| C(6)-C(7)-C(8) | 101.6(4) | O(8)-C(8)-C(9) | 115.1(4) |
| O(8)-C(8)-C(7) | 115.2(5) | C(9)-C(8)-C(7) | 104.2(4) |
| N(1)-C(9)-C(8) | 106.1(4) | | |

Hydrogen coordinates ($\times 10^4$) and isotropic displacement parameters ($\text{\AA}^2 \times 10^3$).

| | x | y | z | U(eq) |
|---|---|---|---|---|
| H(1) | 3134(6) | 5285(5) | 2897(3) | 47(5) |
| H(21) | 576(6) | 3329(8) | 3217(4) | 47(5) |
| H(22) | 649(6) | 4493(8) | 2359(4) | 47(5) |
| H(31) | 734(7) | 6607(9) | 3391(4) | 47(5) |
| H(32) | −763(7) | 5610(9) | 3650(4) | 47(5) |
| H(41) | 500(7) | 4576(8) | 4946(4) | 47(5) |
| H(42) | 649(7) | 6384(8) | 5010(4) | 47(5) |
| H(5) | 3314(7) | 6299(8) | 4509(4) | 47(5) |
| H(50) | 4162(6) | 4997(78) | 5719(12) | 53(12) |
| H(6) | 2800(6) | 3046(6) | 4295(4) | 47(5) |
| H(7) | 5539(7) | 3146(6) | 4477(3) | 47(5) |
| H(70) | 6500(64) | 5262(47) | 4122(18) | 53(12) |
| H(8) | 4709(7) | 1523(6) | 3307(4) | 47(5) |
| H(80) | 6686(42) | 3168(27) | 2298(40) | 53(12) |
| H(91) | 4020(9) | 3629(8) | 2887(4) | 47(5) |
| H(92) | 2914(9) | 2313(8) | 2295(4) | 47(5) |

TABLE 4

Stability of SW Hydrochloride, SW Free Base and SW Hydrobromide

| Condition | SW-HCL | SW | Hydrobromide |
|---|---|---|---|
| (a) | 99.4% | 99.3% | 71.1% |
| (b) | 100.9% | 20.0%* | 88.3% |
| (c) | 101.2% | 9.7%* | 92.1% |
| (d) | 103.2% | 98.5% | 95.5% |
| (e) | 101.9% | 102.5% | 91.4% |

TABLE 3

| Publication | Model |
|---|---|
| (Dennis, Cancer Res. 46:5131,1986) | MDAY-D2 murine lymphoreticular tumor cell model (metastasis); and Immune-intact mice inoculated with B16-F10 murine melanoma cells |
| DeSantis et al, Biophys. Res. Commun. 142:348, 1989 | NIH 3T3 fibroblasts transfected with human tumour DNA from T-24 bladder cancer sarcoma cells (al-l) grown in soft agar |
| Grzegorzewski et al, Cancer Comm. 1:373, 1989 | Murine mastocytoma cell line P-815 used in vitro and in vivo (immune-intact mice) |
| Galustian et al, Immunopharm. 27:165. 1994 | Human peripheral blood mononuclear cells in culture with human eythroblastoid, K562 NK-sensitive target) and human colorectal, CoLo 320 (LAK-sensitive target) tumor cell lines |
| Mohla et al, Anticancer Res. 10:1515, 1990 | MCF-7 (estrogen receptor-negative) and MDA-MB-231 (estrogen receptor-positive) human breast carcinoma cells injected into athymic nude mice |
| Dennis et al, Cancer Res. 50:1867-1872, 1990 | Athymic nude mice implanted with human MeWo melanoma (which expresses the highly branched, complex-type N-linked oligosaccharides) cells or 3S5 (glycosylation mutant of MeWo, which has a defect in complex-type N-linked oligosaccharide processing) |
| Kino et al, Journal Antibiot. (Tokyo) 38:936, 1985 | Immunodeficient mouse inoculated with murine sarcoma 180 ascites tumor, murine B16 melanoma cells |
| Korczak et al, Adv. Exp. Med. Biol. 353:95, 1994 | Spi murine mammary carcinoma in immune-intact mice |
| Newton et al, J. Natl. Cancer Ins., 81:1024, 1989 | Immune-intact mice inoculated with B16-BL6 murine melanoma cells or M5076 murine reticulum sarcoma tumour cells |
| Humphries et al, Cancer Res. 48:1410, 1988 | B16-F10 murine melanoma cells administered to immune-intact mice and experimentally produced (GM1 antibody- or cyclophosphamide-treated) and genetically mutated (homozygous beige mice) NK-deficient mice |
| Dennis et al, Oncogene 4:853, 1989 | HT29m human colon carcinoma cells injected into athymic mice |

TABLE 5

Other physical properties of Swainsonine Hydrochloride (SW = swainsonine)

| Condition | SW-HCl | SW-HBr | SW-HF | Free base |
|---|---|---|---|---|
| Melting point | 190.8–191.6° C. | 151.1–153.1° C.<br>151.4-153.80C | decomposes without melting | 146.0–147.0° C.<br>146.0–146.7° C. |
| Thermal decomposition | 230° C. | 210° C. | 152° C. | 140° C. |
| Crystallinity | colourless crystals, orthorhombic unit cell, having the space group $P_{2_12_12}$. The cell dimensions are a = 8.09, b = 9.39 and c = 13.62 A | colourless crystals | colourless needles | Fluffy colourless fibers |
| Solubility in distilled water at room temperature | 3 g/mL | not done | not done | 0.8 g/mL |

TABLE 6

BEST SQUARES PLANES
Atom Deviations from Plane

Swainsonine hydrochloride (Plane Defined by N1, C9, C8, C7)

| N1 | 0.052 Å | |
|---|---|---|
| C9 | −0.079 | Rms 0.066 |
| C8 | 0.078 | |
| C7 | −0.050 | |
| C6 | 0.0671 Å | out of the above plane |

Swainsonine Diaeetate

| N1 | −0.023 Å | |
|---|---|---|
| C9 | 0.034 | Rms 0.029 |
| CB | −0.034 | |
| C7 | 0.022 | |
| C6 | 0.644 Å | out of above plane |

Swainsonine Hydrobromide

| N1 | 0.042 Å | |
|---|---|---|
| C9 | −0.064 | Rms 0.053 |
| C8 | 0.062 | |
| C7 | −0.040 | |
| C6 | 0.673 Å | out of above plane |

TABLE 7

$^1$H chemical shifts of samples SW and SWHCl in $D_2O$.

| PROTON | CHEMICAL SHIFT (ppm) | |
|---|---|---|
| | SW | SWHCl |
| 1 | 4.125 | 4.368 |
| 2 | 4.217 | 4.509 |
| 3[a] | 2.754 | 3.306 |
| 3'[a] | 2.420 | 3.379 |
| 5e[b] | 2.775 | 3.417 |
| 5a | 1.826 | 2.805 |
| 6e | 1.587 | 1.904 |
| 6a | 1.384 | 1.639 |
| 7e | 1.927 | 2.088 |
| 7a | 1.105 | 1.387 |

TABLE 7-continued $^1$H chemical shifts of samples SW and SWHCl in $D_2O$.

| PROTON | CHEMICAL SHIFT (ppm) | |
|---|---|---|
| | SW | SWHCl |
| 8 | 3.668 | 3.931 |
| 9 | 1.785 | 2.959 |

[a]Protons 3 and 3' correspond to the pseudo-equatorial and pseudo-axial positions, respectively, in the five-membered ring.
[b]Estimated chemical shift owing to overlap with H-3 in SW and H-3' in SWHCl.

TABLE 8

Selected $^1$H—$^1$H coupling constants of samples SW and SWHCl in $D_2O$.

| PROTONS | COUPLING CONSTANT (Hz) | |
|---|---|---|
| | SW | SWHCl |
| $^3J$ | | |
| 1, 2 | 5.9 | 4.7 |
| 1, 9 | 3.7 | 2.6 |
| 2, 3 | 2.5 | 4.6 |
| 2, 3' | 7.9 | 9.0 |
| 5a, 6e | 2.9 | 3.4 |
| 5a, 6a | 11.5 | 12.5 |
| 8, 7e | 4.7 | 4.5 |
| 8, 7a | 9.5 | 10.7 |
| 8, 9 | 11.1 | 10.2 |
| $^2J$ | | |
| 3, 3' | −11.0 | −12.7 |
| 5e, 5a | −12.5 | −12.8 |
| $^5J$ | | |
| 1, 5e | | 0.7 |

TABLE 9

¹³C Chemical shifts of samples SW and SWHCl in D₂O.

| | CHEMICAL SHIFT (ppm) | |
|---|---|---|
| CARBON | SW | SWHCl |
| 1 | 69.4 | 68.1 |
| 2 | 68.7 | 68.1 |
| 3 | 60.3 | 58.1 |
| 5 | 51.3 | 51.3 |
| 6 | 22.9 | 21.1 |
| 7 | 32.2 | 30.6 |
| 8 | 66.0 | 63.7 |
| 9 | 72.5 | 72.0 |

TABLE 10

Summary table of carbon NMR and APT band assignments.

| Chemical Shift (δ) (ppm) | Number of carbons | APT C - Types | Tentative Assignments |
|---|---|---|---|
| 21.14 | 1 | CH2 | 6 |
| 30.60 | 1 | CH2 | 7 |
| 51.29 | 1 | CH2 | 5 |
| 58.14 | 1 | CH2 | 3 |
| 63.67 | 1 | CH | 8 |
| 68.05 | 2 | CH | 1,2 |
| 71.95 | 1 | CH | 9 |

TABLE 11

Summary table of quantitative microanalytical results
Swainsonine Hydrochloride

| | Theory for C₁₈H₁₆ClNO₃ | Found for Lot SCR |
|---|---|---|
| % Carbon (1) | 45.83 | 45.89 |
| % Hydrogen (1) | 7.69 | 7.88 |
| % Nitrogen (1) | 6.68 | 6.73 |
| % Chlorine (2) | 16.91 | 17.21 |
| % Oxygen (3) | 22.89 | 22.29 |
| % Moisture (4) | 0.00 | 0.21 |
| % Residual Solvents (5) | | |
| % Isopropyl Alcohol | 0.000 | 0.203 |
| % Ethanol | 0.000 | ND |
| % Tetrahydrofuran | 0.000 | ND |
| % Toluene | 0.000 | ND |
| % Ash Content (6) | 0.00 | 0.02 |

(1) Determined by combustion analysis (TP 10812).
(2) Determined by potentiometric titration analysis (TP 10812).
(3) Calculated by difference.
(4) Determined by Coulometric Karl Fischer Titration at Phoenix Labs.
(5) Determined by Headspace GC Analysis (In all there were 16 organic solvents tested for by Phoenix Labs), ND = None Detected.
(6) Determined by U.S.P. <281>, Residue on Ignition (TP 18038).

Table 12

Summary table of Infrared band assignments.

| Frequency (cm-1) | Tentative Assignment |
|---|---|
| 3300–3500 | —O—H stretch (alcohol) |
| 3150–3300 | —N—H stretch (amine) |
| 2800–3050 | —C—H stretch (aliphatic) |
| 3007 | —C—H asym. stretch (methylene) |
| 2850 | —C—H sym. stretch (methylene) |
| 2769 | —N—H stretch (tertiary amine salt) |
| 1646 | —N—H asym. deformation (amine salt) |
| 1462 | —C—H sym. bend (cyclohexane) |
| 1442 | —C—H sym. bend (cyclopentane) |
| 1412 | —O—H in plane bend (alcohol) |
| 1354 | —Q—H in plane bend (alcohol) |
| 1308 | —N—H sym. deformation (amine salt) |
| 1000–1250 | —C—C and —C—N stretch |
| 1090 | —C—O stretch (secondary alcohol) |
| 894 | —C—H rock |
| 848 | —N—H wag |
| 749 | —C—C skeletal vibrations |

TABLE 13

Summary of Mass Spectral fragmentation scheme.

| CI(CH₄) | Possible Assignment |
|---|---|
| 174 | M + 1 (Parent, Free Base) |
| 156 | M – 18 (loss of (H2O)) |
| 138 | M – 36 (loss of 2(H2O)) |
| 120 | M – 54 (loss of 3(H2O)) |
| 113 | M – 61 (loss of C₂H₅N + H₂O) |

TABLE 14

The effect of SW or SWHCl on the growth of early erythroid colonies from $2 \times 10^5$ nucleated BM cells.

| | | Treatment in vitro | | | |
|---|---|---|---|---|---|
| | | Swainsonine | | Swainsonine HCl | |
| Mouse | control | 0.3 μg/ml | 3 μg/ml | 0.3 μg/ml | 3 μg/ml |
| 1(control) | *54 ± 12 | 108 ± 21 | 101 ± 12 | 75 ± 16 | 87 ± 16 |
| p** | | <0.029 | <0.008 | <0.136 | <0.045 |
| 2(GD0039 treated) | 22 ± 5 | 71 ± 15 | 103 ± 1 | 97 ± 4 | 127 ± 18 |
| p | | <0.017 | <0.001 | <0.00002 | <0.001 |

*Data are mean CFU-E of triplicate counts ± SD.
**p, different from control in two-tailed Student's t-test.

We claim:

1. A stable crystalline chloride or bromide salt of swainsonine.

2. A crystalline chloride salt of swainsonine as claimed in claim 1 comprising molecules of chloride salts of swainsonine held together by hydrogen bond interactions.

3. A crystalline bromide salt of swainsonine as claimed in claim 1 comprising molecules of bromide salts of swainsonine held together by hydrogen bond interactions.

4. A crystalline chloride or bromide salt of swainsonine as claimed in claim 1 comprising four molecules of swainsonine chloride or bromide salts in a unit cell.

5. A crystalline chloride or bromide salt of swainsonine as claimed in claim 1, comprising molecules of hydrochloride or hydrobromide salts of swainsonine.

6. A crystalline hydrochloride salt of swainsonine as claimed in claim 5 wherein the molecules of hydrochloride salt of swainsonine are held together by hydrogen bond interactions from the nitrogen and oxygen atoms of a first molecule of a hydrochloride salt of swainsonine to chloride ions of other molecules of a hydrochloride salt of swainsonine.

7. A crystalline hydrobromide salt of swainsonine as claimed in claim 5 wherein the molecules of hydrobromide salt of swainsonine are held together by hydrogen bond interactions from the oxygen atoms of a first molecule of a hydrobromide salt of swainsonine to bromide ions of other molecules of a hydrobromide salt of swainsonine, and a hydrogen bond interaction from the nitrogen atom of the first molecule to an oxygen atom of a second molecule of a hydrobromide salt of swainsonine.

8. A crystalline chloride or bromide salt of swainsonine as claimed in claim 1 which has the space group symmetry $P2_12_12_1$.

9. A crystalline hydrochloride or hydrobromide salt of swainsonine as claimed in claim 5 which has the space group symmetry $P2_12_12_1$.

10. A crystalline hydrochloride or hydrobromide salt of swainsonine as claimed in claim 9 wherein the unit cell is orthorhombic.

11. A crystalline hydrochloride salt of swainsonine as claimed in claim 10 which has the unit cell lengths: a=8.09±0.01 Å, b=9.39±0.01 Å, and c=13.621±0.01 Å.

12. A crystalline hydrobromide salt of swainsonine as claimed in claim 10 which has the unit cell lengths: a=8.40±0.01 Å, b=8.63±0.01 Å, c=14.12±0.01 Å.

13. A crystalline hydrochloride salt of swainsonine as claimed in claim 11 having the atomic coordinates as shown in Table 1.

14. A crystalline hydrobromide salt of swainsonine as claimed in claim 12 having the atomic coordinates as shown in Table 2.

15. A composition comprising a stable crystalline chloride or bromide salt of swainsonine and a pharmaceutically acceptable carrier.

16. A composition as claimed in claim 15 wherein the chloride or bromide salt is a hydrochloride or hydrobromide salt.

17. A method for preparing a crystalline hydrochloride salt of swainsonine as claimed in claim 5 comprising treating swainsonine acetonide with hydrochloride acid, and purifying the halide salt by crystallization and without chromatography to yield a crystalline hydrochloride salt of swainsonine.

18. A method for stimulating the immune system, treating proliferative disorders, or microbial or parasitic infections in a subject comprising administering to a subject an effective amount of a composition as claimed in claim 15.

19. A method for the treatment of cancer comprising administering to a subject an effective amount of a composition as claimed in claim 15.

20. A method as claimed in claim 19 wherein the treatment comprises inhibiting metastasis or neoplastic growth.

21. A method for stimulating hematopoietic progenitor cell growth comprising administering to a subject an effective amount of a composition as claimed in claim 15.

22. A method as claimed in claim 21 wherein the patient has been administered a myelosuppressive agent or is a bone marrow transplant recipient.

23. A method for treating a viral, bacterial, fungal, or parasitic infection in which clearance of pathogen requires a Th1 response in a subject comprising administering to a subject an effective amount of a composition as claimed in claim 15.

24. A method of treating hepatitis C comprising administering to a subject an effective amount of a composition formulated from swainsonine free base, a halide salt of swainsonine, or a combination thereof.

25. A method of augmenting immunogenicity of a vaccine comprising administering a stable crystalline chloride or bromide salt of swainsonine as claimed in claim 1.

26. A method of computationally evaluating a chemical entity for inhibition of Golgi α-mannosidase II comprising modeling the properties of said entity using atomic coordinates of the purified crystalline chloride or bromide salt of swainsonine as claimed in claim 1 or portions thereof.

27. A stable crystalline chloride salt of swainsonine of claim 1.

28. A swainsonine salt of claim 27 which is substantially purified.

29. A composition of claim 15 further comprising a different antiproliferative agent, antimicrobial agent, immunostimulatory agent of anti-inflammatory agent.

30. A crystalline chloride or bromide salt of swainsonine having long-term stability to UV light, oxidation, heat and humidity.

31. A crystalline chloride salt of swainsonine of claim 30.

32. A method of claim 19 wherein said cancer is renal, head, neck, colon or rectal cancer.

33. An isolated, stable crystalline chloride or bromide salt of swainsonine.

* * * * *